US009125939B2

(12) United States Patent
Kikuchi et al.

(10) Patent No.: US 9,125,939 B2
(45) Date of Patent: Sep. 8, 2015

(54) CARBOSTYRIL DERIVATIVES AND MOOD STABILIZERS FOR TREATING MOOD DISORDERS

(75) Inventors: Tetsuro Kikuchi, Tokushima (JP); Taro Iwamoto, Princeton, NJ (US); Tsuyoshi Hirose, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 800 days.

(21) Appl. No.: 10/556,600

(22) PCT Filed: May 19, 2004

(86) PCT No.: PCT/US2004/013308
§ 371 (c)(1),
(2), (4) Date: Aug. 2, 2006

(87) PCT Pub. No.: WO2004/105682
PCT Pub. Date: Dec. 9, 2004

(65) Prior Publication Data
US 2007/0031513 A1 Feb. 8, 2007

Related U.S. Application Data

(60) Provisional application No. 60/473,378, filed on May 23, 2003.

(51) Int. Cl.
| A61K 31/47 | (2006.01) |
| A61K 31/44 | (2006.01) |
| A61K 33/14 | (2006.01) |
| A01N 59/08 | (2006.01) |
| A61K 45/06 | (2006.01) |
| A61K 31/19 | (2006.01) |
| A61K 31/195 | (2006.01) |
| A61K 31/425 | (2006.01) |
| A61K 31/4704 | (2006.01) |
| A61K 31/496 | (2006.01) |
| A61K 31/497 | (2006.01) |
| A61K 31/55 | (2006.01) |
| A61K 31/7008 | (2006.01) |
| A61K 33/00 | (2006.01) |

(52) U.S. Cl.
CPC .............. *A61K 45/06* (2013.01); *A61K 31/19* (2013.01); *A61K 31/195* (2013.01); *A61K 31/425* (2013.01); *A61K 31/4704* (2013.01); *A61K 31/496* (2013.01); *A61K 31/497* (2013.01); *A61K 31/55* (2013.01); *A61K 31/7008* (2013.01); *A61K 33/00* (2013.01); *A61K 33/14* (2013.01)

(58) Field of Classification Search
CPC ............ A61K 31/4704; A61K 31/496; A61K 31/497; A61K 33/00; A61K 33/44; A61K 2300/00
USPC .................. 514/310, 557, 299, 722; 424/722
See application file for complete search history.

(56) References Cited

U.S. PATENT DOCUMENTS

| 5,006,528 A | 4/1991 | Oshiro et al. |
| 2001/0023254 A1 | 9/2001 | McElroy |
| 2002/0173513 A1 | 11/2002 | Jordan et al. |
| 2003/0027817 A1 | 2/2003 | Tollefson |
| 2003/0109546 A1 | 6/2003 | Fenton |
| 2005/0004106 A1 | 1/2005 | Romano |

FOREIGN PATENT DOCUMENTS

| EP | 0367141 A2 | 9/1990 |
| EP | 0966967 A2 | 12/1999 |
| WO | WO 97/35584 A1 | 10/1997 |
| WO | WO 99/62522 A1 | 12/1999 |
| WO | WO 00/59489 A2 | 10/2000 |
| WO | WO 02/060423 A2 | 8/2002 |
| WO | WO 02/087590 A1 | 11/2002 |
| WO | WO 03/026659 | 4/2003 |
| WO | WO 03/066039 A1 | 8/2003 |
| WO | WO 2004060374 A1 | 7/2004 |
| WO | WO 2004/100992 A2 | 11/2004 |

OTHER PUBLICATIONS

CN138-00ST, Apr. 2003.*
RU Search Report dated Nov. 8, 2006 issued in Patent Application No. 2004 009073.
Borwin Bandelow and Andreas Meier; Aripiprazole, a "Dopamine-Serotonin System Stabilizer" in the Treatment of Psychosis; German Journal of Psychiatry, vol. 6, No. 1, 2003; pp. 9-16.
Melissa P. Delbello, M. D., et al.; A Double-Blind, Randomized, Placebo-Controlled Study of Quetiapine as Adjunctive Treatment for Adolescent Mania; Journal of the American Academy of Child and Adolescent Psychiatry, vol. 41, No. 10, 2002, pp. 1216-1223.
Mauricio Tohen, M.D. et al.; Efficacy of Olanzapine in Combination with Valproate or Lithium in the Treatment of Mania in Patients Partially Nonresponsive to Valproate or Lithium Monotherapy; Archives of General Psychiatry, vol. 59, No. 1, 2002, pp. 62-69.
Frank I. Tarazi, et al., Long-term effects of olanzapine, risperidone, and quetiapine on serotonin 1A, 2A and 2C receptors in rat forebrain regions; Psychopharmacology, vol. 161, No. 3, 2002, pp. 263-270.

(Continued)

Primary Examiner — Shobha Kantamneni
(74) Attorney, Agent, or Firm — Finnegan, Henderson, Farabow, Garrett & Dunner LLP

(57) ABSTRACT

The pharmaceutical composition of the present invention comprises a carbostyril derivative which is a dopamine-serotonin system stabilizer and a mood stabilizer in a pharmaceutically acceptable carrier. The carbostyril derivative may be aripiprazole or a metabolite thereof. The mood stabilizer may include but is not limited to lithium, valproic acid, divalproex sodium, carbamaza-pine, oxcarbamazapine, zonisamide, lamotragine, topiramate, gabapentin, levetiracetam or clonazepam. These compositions are used to treat patients with mood disorders, particularly bipolar disorder with or without psychotic features, mania or mixed episodes. Methods are provided for separate administration of a carbostyril derivative and a mood stabilizer to a patient with a mood disorder.

10 Claims, 8 Drawing Sheets

(56) References Cited

OTHER PUBLICATIONS

Merck Index 13, the Merck & Co. NJ. USA document, No. 791, 1788, 5368, 9625, 4342 and 2413, year 2001.

The Merck Index, An Encyclopedia of Chemicals, Drugs and Biologicals, Thirteenth Edition, Merck Index & Co., NJ, USA document, No. 791, 2001 (year).

The Merck Index, An Encyclopedia of Chemicals, Drugs and Biologicals, Thirteenth Edition, Merck Index & Co., NJ, USA document, No. 1788, 2001 (year).

The Merck Index, An Encyclopedia of Chemicals, Drugs and Biologicals, Thirteenth Edition, Merck Index & Co., NJ, USA document, No. 5368, 2001 (year).

The Merck Index, An Encyclopedia of Chemicals, Drugs and Biologicals, Thirteenth Edition, Merck Index & Co., NJ, USA document, No. 9625, 2001 (year).

The Merck Index, An Encyclopedia of Chemicals, Drugs and Biologicals, Thirteenth Edition, Merck Index & Co., NJ, USA document, No. 4342, 2001 (year).

The Merck Index, An Encyclopedia of Chemicals, Drugs and Biologjcals, Thirteenth Edition, Merck Index & Co., NJ, USA document, No. 2413, 2001 (year).

Gordon et al., Mood Stabilization and weight loss with Topiramate, American Journal of Psychiatry, Jun. 1999, vol. 156, No. 6, pp. 968-969, see pp. 1 and 2.

Baldessarini et al, Hospital Use of Antipsychotic Agents in 1989 and 1993: Stable Dosing with Decreased Length of Stay, American Journal of Psychiatry, Jul. 1995, vol. 152, No. 7, pp. 1038-1044, see pp. 1-8.

Jacobsen et al., Risperidone in the Treatment of Affective Illness and Obsessive-Compulsive Disorder, Journal of Clinical Psychiatry, Sep. 1995, vol. 56, No. 9, pp. 423-429.

Weisler et al., Adjunctive Use of Olanzapine in Mood Disorders: Five Case Reports, Annals of Clinical Psychiatry, 1997, vol. 9, No. 4, pp. 259-262.

Mcelroy et al., Clozapine in the Treatment of Psychotic Mood Disorders, Schizoaffective Disorder, and Schizophrenia, J. Clin. Psychiatry, Oct. 1991, vol. 52, No. 10, pp. 411-414.

Citrome et al., Pharmacokinetics and Safety of Aripiprazole and Concomitant Mood Stabilizers, 2002, vol. 5, Suppl. 1, p. S187 (P.4.E. 035).

Moeller et al., Treatment of Bipolar Disorder, J. Clin. Psychiatry, 2003, vol. 64, Suppl. 6, pp. 9-17.

Kowatch et al., The Use of Mood Stablizers and Atypical Antipsychotics in Children and Adolescents with Bipolar Disorders, CNS Spectrums, Apr. 2003, vol. 8, No. 4, pp. 273-280.

Shin Shiah et al., "Serotonin in Mania and in the Mechanism of Action of Mood Stabilizers: A Review of Clinical Studies", Bipolar Disorders: An International Journal of Psychiatry and Neurosciences; Dec. 24, 2001; Abstract; vol. 2, issue 2.

Bobula et al., "Adaptive Changes in the Reactivity of $5\text{-}HT_{1A}$ and $5\text{-}HT_2$ Receptors Induced in Rat Frontal Cortex by Repeated Imipramine and Citalopram", Naunyn-Schmiedeberg's Arch Pharmacol, 2003, pp. 444-450, 367.

Ichikawa et al., "Valproate and Carbamazepine Increase Prefrontal Dopamine Release by $5\text{-}HT_{1A}$ Receptor Activation", European Journal of Pharmacology, 1999, pp. R1-R3, 367.

Brambilla et al., "Atypical Antipsychotics and Mood Stabilization in Bipolar Disorder", Psychopharmacologia, 2003, pp. 315-332, vol. 166 No. 4.

Robert M. Post et al., "Acute and prophylactic effects of anticonvulsants in bipolar depression", Clinical Neuroscience Research 2 (2002) 228-2511.

Yasuhiro Suzuki, "Zonisamide in West syndrome", Brain and development 23 (2001), 658-661.

English Translation of Egyptian Office Action dated Jun. 27, 2010.

Casey, Daniel, E., "Switching Patients to Aripiprazole From Other Antipsychotic Agents a Multicenter Randomized Study", Psychopharmacology (2003), 166, pp. 390-399.

\* cited by examiner

CARBOSTYRIL DERIVATIVES AND MOOD STABILIZERS FOR TREATING MOOD DISORDERS

CROSS-REFERENCE TO RELATED APPLICATION

This Application is a 371 of PCT/US2004/013308, filed May 19, 2004, which claim priority to U.S. Provisional Application No. 60/473,378, filed May 23, 2003; the disclosures of which are incorporated herein by reference.

FIELD OF THE INVENTION

The present invention provides pharmaceutical compositions comprising carbostyril derivatives that act as dopamine-serotonin system stabilizers in combination with mood stabilizers in a pharmaceutically acceptable carrier. The present invention provides methods to treat mood disorders such as bipolar disorder with or without psychotic features, mania or mixed episodes using the compositions of the present invention or by separately administering these carbostyril derivatives and mood stabilizers. The carbostyril derivatives of the present invention include but are not limited to aripiprazole and metabolites thereof, such as dehydroaripiprazole. The mood stabilizers include, but are not limited to, lithium, valproic acid, divalproex sodium, carbamazepine, oxcarbamazapine, zonisamide, lamotragine, topiramate, gabapentin, levetiracetam and clonazepam.

BACKGROUND OF THE INVENTION

The number of people with mood disorders, such as bipolar disorder with or without psychotic features, mania or mixed episodes is increasing every year for numerous reasons. Since the period of 1950, tricyclic antidepressant drugs (e.g., imipramine, desipramine, amitriptyline, etc.) have been developed that act to inhibit monoamine reuptake. They are frequently used for treating patients suffering from mood disorders. However, these drugs have side-effects, such as the following: dry mouth, hazy eyes, dysuria, constipation, recognition disturbance and the like due to anticholinergic activity; cardiovascular side-effects such as, orthostatic hypotension, tachycardia and the like on the basis of $\alpha_1$-adrenoreceptor antagonist activity; side-effects such as, sedation, increase in the body weight and the like on the basis of histamine-$H_1$ receptor antagonist activity.

Although the mood disorders including bipolar disorder with or without psychotic features, mania or mixed episodes are heterogeneous diseases, and the causes of these diseases are not fully understood, it is likely that the abnormalities of the monoaminergic central nervous system caused by serotonin, norepinephrine and dopamine and the like, and the abnormality of various hormones and peptides as well as various stressors are causes of depression and various other mood disorders (Kubota Masaharu et al.: "RINSHOU SEISHIN IGAKU" Vol. 29, pp 891-899, (2000)). For these reasons, even though mood stabilizer drugs, such as lithium, valproic acid, divalproex sodium, carbamazepine, oxcarbamazepine, zonisamide, lamotragine, topiramate, gabapentin, levetiracetam and clonazepam have been used, these drugs are not always effective in treating all patients.

New therapeutic trials involve proposed combined therapies using an atypical antipsychotic drug, such as olanzepine or quetiapine, which are agents for treating schizophrenia (anti-psychotic drug), together with mood stabilizing drug such as valproate, lithium or divalproex ((Arch. Gen. Psychiatry, 2002 January 59:1):62-69; J Am Acad Child Adolesc Psychiatry 2002 October; 41(10) :1216-23.)

Further, commercially available atypical antipsychotic drugs have significant problems relating to their safety. For example, clozapine, olanzapine and quetiapine increase body weight and enhance the risk of diabetes mellitus (Newcomer, J. W. (Supervised Translated by Aoba Anri): "RINSHOU SEISHIN YAKURI" Vol. 5, pp 911-925, (2002), Haupt, D. W. and Newcomer, J. W. (Translated by Fuji Yasuo and Misawa Fuminari): "RINSHOU SEISHIN YAKURI" Vol. 5, pp 1063-1082, (2002)). In fact, urgent safety alerts have been issued in Japan relating to hyperglycemia, diabetic ketoacidosis and diabetic coma caused by olanzapine and quetiapine, indicating that these drugs were subjected to dosage contraindication to the patients with diabetes mellitus and patients having anamnesis of diabetes mellitus. Risperidone causes increases serum prolactin levels and produces extrapyramidal side effects at high dosages. Ziprasidone enhances the risk of severe arrhythmia on the basis of cardio-QTc prolongation action. Further, clozapine induces agranulocytosis, so that clinical use thereof is strictly restricted (van Kammen, D. P. (Compiled under Supervision by Murasaki Mitsuroh) "RINSHOU SEISHIN YAKURI" Vol. 4, pp 483-492, (2001)).

Accordingly what is needed are new compositions useful for treating mood disorders, particularly bipolar disorder with or without psychotic features, mania or mixed episodes, which are efficacious and do not cause the deleterious side effects associated with prior art compounds.

SUMMARY OF THE INVENTION

The present invention solves the problems described above by providing novel compositions and methods of using these compositions for treating mood disorders, particularly bipolar disorder, including but not limited to bipolar disorder I, bipolar disorder II, bipolar disorder with and without psychotic features, and mania, acute mania, bipolar depression or mixed episode.

The present invention provides solutions to the above-mentioned problems, and demonstrates that the mood disorders, such as bipolar disorder and mania, can be treated effectively by administering to a patient with such disorder a composition comprising at least one carbostyril derivative that is a dopamine-serotonin system stabilizer in combination with at least one mood stabilizer in a pharmaceutically acceptable carrier. A preferred carbostyril derivative of the present invention that is a dopamine-serotonin system stabilizer is aripiprazole or a metabolite thereof. Another preferred carbostyril derivative of the present invention that is a dopamine-serotonin system stabilizer is a metabolite of aripiprazole called dehydroaripiprazole, also known as OPC-14857. Other such metabolites of aripiprazole included within the present invention are shown in FIG. 8. Preferred aripiprazole metabolites are shown in FIG. 8 indicated by the following designations: OPC-14857, DM-1458, DM-1451, DM-1452, DM-1454 and DCPP.

Aripiprazole, also called 7-{4-[4-(2,3-dichlorophenyl)-1-piperazinyl]butoxy}-3,4-dihydro-2(1H)-quinolinone, is a carbostyril and is useful for treating schizophrenia (JP-A-2-191256, U.S. Pat. No. 5,006,528). Aripiprazole is also known as 7-[4-[4-(2,3-dichlorophenyl)-1-piperazinyl]butoxy]-3,4-dihydrocarbostyril, Abilify, OPC-14597, OPC-31 and BMS-337039. Aripiprazole possesses 5-$HT_{1A}$ receptor agonist activity, and is known as a useful compound for treating types of depression and refractory depression, such as endogenous depression, major depression, melancholia and the like (WO 02/060423A2; Jordan et al U.S. Patent Application 2002/

0173513A1)). Aripiprazole has activity as an agonist at serotonin receptors and dopamine receptors, and acts as an agonist or partial agonist at the serotonin $5HT_{1A}$ receptor and as an agonist or partial agonist at the dopamine $D_2$ receptor. Aripiprazole is a dopamine-serotonin system stabilizer. Metabolites of aripiprazole are included within the scope of the present invention. One such metabolite of aripiprazole is called dehydroaripiprazole. Other such metabolites of aripiprazole included within the present invention are shown in FIG. 8. Preferred metabolites are shown in FIG. 8 indicated by the following designations: OPC-14857, DM-1458, DM-1451, DM-1452, DM-1454 and DCPP.

The at least one mood stabilizer used in the present invention includes but is not limited to the following: lithium, valproic acid, divalproex sodium, carbamazapine, oxcarbamazapine, zonisamide, lamotragine, topiramate, gabapentin, levetiracetam and clonazepam.

The novel compositions of the present invention comprising a carbostyril derivative with activity as a dopamine-serotonin system stabilizer and at least one mood stabilizer in a pharmaceutically acceptable carrier may be combined in one dosage form, for example a pill. Alternatively the carbostyril derivative with activity as a dopamine-serotonin system stabilizer and the at least one mood stabilizer may be in separate dosage forms, each in a pharmaceutically acceptable carrier. These compositions are administered to a patient with a mood disorder, such as bipolar disorder or mania, in an amount and dose regimen effective to treat the mood disorder.

Accordingly, it is an object of the present invention to provide a composition useful for treating a mood disorder.

It is an object of the present invention to provide a composition useful for treating a mood disorder, wherein the mood disorder is bipolar disorder.

It is an object of the present invention to provide a composition useful for treating a mood disorder, wherein the mood disorder is mania.

It is another object of the present invention to provide a composition comprising a carbostyril derivative with activity as a dopamine-serotonin system stabilizer and at least one mood stabilizer in a pharmaceutically acceptable carrier.

Yet another object of the present invention is to provide a composition comprising a carbostyril derivative with activity as a dopamine-serotonin system stabilizer and at least one mood stabilizer in a pharmaceutically acceptable carrier, wherein the carbostyril derivative is aripiprazole or a metabolite thereof.

Yet another object of the present invention is to provide a composition comprising a carbostyril derivative with activity as a dopamine-serotonin system stabilizer and at least one mood stabilizer, wherein the carbostyril derivative with activity as a dopamine-serotonin system stabilizer is a metabolite of aripiprazole and is OPC-14857, DM-1458, DM-1451, DM-1452, DM-1454 or DCPP.

Yet another object of the present invention is to provide a composition comprising a carbostyril derivative with activity as a dopamine-serotonin system stabilizer and at least one mood stabilizer, wherein the carbostyril derivative is dehydroaripiprazole.

It is an object of the present invention to provide a method for treating a mood disorder.

It is an object of the present invention to provide a method for treating a mood disorder wherein the mood disorder is bipolar disorder.

It is an object of the present invention to provide a method for treating a mood disorder wherein the mood disorder is mania.

It is another object of the present invention to provide a method for treating a mood disorder comprising administration to a patient with a mood disorder of a composition comprising a carbostyril derivative with activity as a dopamine-serotonin system stabilizer and at least one mood stabilizer in a pharmaceutically acceptable carrier.

Yet another object of the present invention is to provide a method for treating a mood disorder comprising administration to a patient with a mood disorder of a composition comprising a carbostyril derivative with activity as a dopamine-serotonin system stabilizer in a pharmaceutically acceptable carrier and a composition comprising at least one mood stabilizer in a pharmaceutically acceptable carrier.

It is another object of the present invention to provide a method for treating a mood disorder comprising administration to a patient with a mood disorder of a composition comprising a carbostyril derivative with activity as a dopamine-serotonin system stabilizer and at least one mood stabilizer together in a pharmaceutically acceptable carrier, wherein the carbostyril derivative is aripiprazole or a metabolite thereof.

Yet another object of the present invention is to provide a method for treating. a mood disorder comprising administration to a patient with a mood disorder of a composition comprising a carbostyril derivative with activity as a dopamine-serotonin system stabilizer in a pharmaceutically acceptable carrier, wherein the carbostyril derivative is aripiprazole or a metabolite thereof, and a composition comprising at least one mood stabilizer in a pharmaceutically acceptable carrier.

Still another object of the present invention is to provide a method for treating a mood disorder comprising administration to a patient with a mood disorder of a composition comprising a carbostyril derivative with activity as a dopamine-serotonin system stabilizer and at least one mood stabilizer in a pharmaceutically acceptable carrier, wherein the carbostyril derivative is a metabolite of aripiprazole and is dehydroaripiprazole (OPC-14857), DM-1458, DM-1451, DM-1452, DM-1454 or DCPP.

Yet another object of the present invention is to provide a method for treating a mood disorder comprising administration to a patient with a mood disorder of a composition comprising a carbostyril derivative with activity as a dopamine-serotonin system stabilizer in a pharmaceutically acceptable carrier, wherein the carbostyril derivative is a metabolite of aripiprazole and is dehydroaripiprazole (OPC-14857), DM-1458, DM-1451, DM-1452, DM-1454 or DCPP, and a composition comprising at least one mood stabilizer in a pharmaceutically acceptable carrier.

Yet another object of the present invention is to provide a method for treating mood disorder comprising administration to a patient with a mood disorder of a composition comprising a carbostyril derivative with activity as a dopamine-serotonin system stabilizer and at least one mood stabilizer in a pharmaceutically acceptable carrier, wherein the mood disorder is bipolar disorder.

Yet another object of the present invention is to provide a method for treating a mood disorder comprising administration to a patient with a mood disorder of a composition comprising a carbostyril derivative with activity as a dopamine-serotonin system stabilizer in a pharmaceutically acceptable carrier and a composition comprising at least one mood stabilizer in a pharmaceutically acceptable carrier, wherein the mood disorder is bipolar disorder.

Yet another object of the present invention is to provide a method for treating mood disorder comprising administration to a patient with a mood disorder of a composition comprising a carbostyril derivative with activity as a dopamine-serotonin system stabilizer and at least one mood stabilizer in a pharmaceutically acceptable carrier, wherein the mood disorder is mania.

Yet another object of the present invention is to provide a method for treating a mood disorder comprising administration to a patient with a mood disorder of a composition comprising a carbostyril derivative with activity as a dopamine-serotonin system stabilizer in a pharmaceutically acceptable carrier and a composition comprising at least one mood stabilizer in a pharmaceutically acceptable carrier, wherein the mood disorder is mania.

It is another object of the present invention to provide a method for treating mood disorder comprising administration to a patient with a mood disorder of a composition comprising a carbostyril derivative with activity as a dopamine-serotonin system stabilizer and at least one mood stabilizer in a pharmaceutically acceptable carrier.

It is another object of the present invention to provide a method for treating mood disorder comprising separate administration to a patient with a mood disorder of a composition comprising a carbostyril derivative with activity as a dopamine-serotonin system stabilizer in a pharmaceutically acceptable carrier, and a composition comprising at least one mood stabilizer in a pharmaceutically acceptable carrier.

It is another object of the present invention to provide a method for treating mood disorder comprising administration to a patient with a mood disorder of a composition comprising a carbostyril derivative with activity as a dopamine-serotonin system stabilizer and at least one mood stabilizer together with a pharmaceutically acceptable carrier, wherein the carbostyril derivative is aripiprazole or a metabolite thereof.

Still another object of the present invention is to provide a method for treating mood disorder comprising administration to a patient with a mood disorder of a composition comprising a carbostyril derivative with activity as a dopamine-serotonin system stabilizer and at least one mood stabilizer in a pharmaceutically acceptable carrier, wherein the carbostyril derivative wherein the carbostyril derivative is a metabolite of aripiprazole and is OPC-14857, DM-1458, DM-1451, DM-1452, DM-1454 or DCPP.

These and other objects, advantages, and uses of the present invention will reveal themselves to one of ordinary skill in the art after reading the detailed description of the preferred embodiments and the attached claims.

DETAILED DESCRIPTION

The pharmaceutical composition of the present invention comprises a first ingredient comprising a carbostyril derivative active as a dopamine-serotonin system stabilizer and a second ingredient comprising a mood stabilizer, in a pharmaceutically acceptable carrier. The pharmaceutical compositions of the present invention are useful in treating mood disorders, including bipolar disorder and mania.

The Pharmaceutical Composition: the First Ingredient

The first ingredient comprises a carbostyril derivative active as a dopamine-serotonin system system stabilizer. Such carbostyril derivative has activity as an agonist or partial agonist at some serotonin receptors and some dopamine receptors, preferably as an agonist or partial agonist at the serotonin 5HT$_{1A}$ receptor and as an agonist or partial agonist at the dopamine D$_2$ receptor. Carbostyril derivatives are described in U.S. Pat. No. 5,006,528 and U.S. published patent application 2002/0173513A1. In one embodiment of the present invention, the carbostyril derivatives represented by the following formula (1) are used:

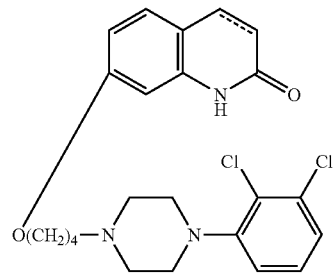

wherein the carbon-carbon bond between 3- and 4-positions in the carbostyril skeleton is a single or a double bond.

In a preferred embodiment, this activity of the carbostyril derivative is as an agonist or partial agonist at the 5HT$_{1A}$ receptor and an agonist or partial agonist at the dopamine D$_2$ receptor subtype. In another preferred embodiment, the carbostyril derivative to be used as a first component in the present invention is aripiprazole, or a metabolic derivative thereof. Metabolic derivatives of aripiprazole include but are not limited to dehydroaripiprazole, also called OPC-14857. Other metabolic derivatives of aripiprazole include but are not limited to the chemical structures shown in FIG. 8 as OPC-14857, DM-1458, DM-1451, DM-1452, DM-1454 and DCPP.

Figure 8:
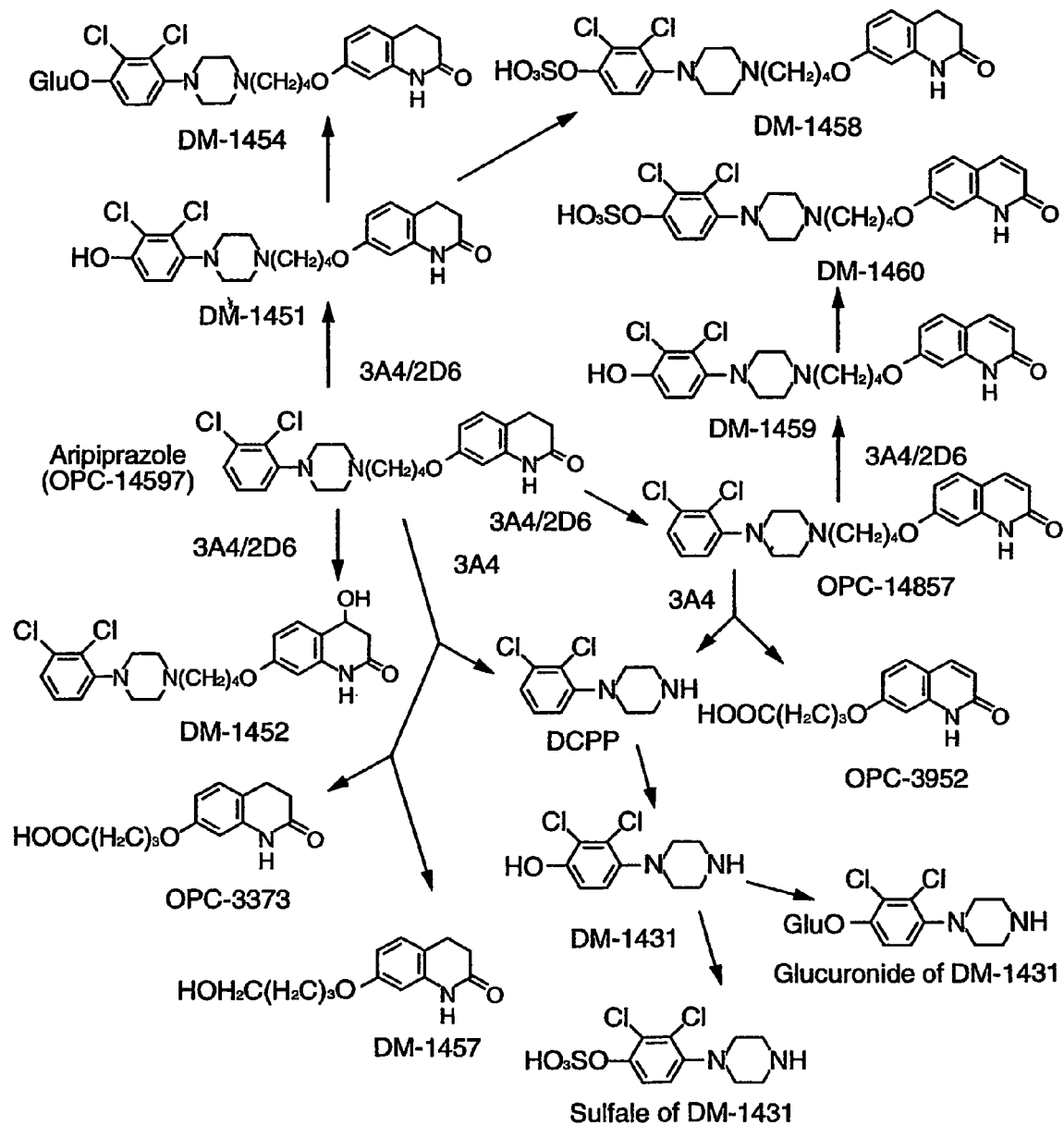
FIG. 8 is a schematic representation of the chemical structures of aripiprazole and metabolites thereof. Some of the metabolites may be formed through other possible pathways; for example, DM-1431 could be formed by N-dealkylation of DM-1451 and DM-1459.

Structures and names of aripiprazole metabolites shown in FIG. 8 are provided below.

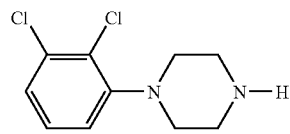

DCPP: 1-(2,3-dichlorophenyl)piperazine, and N-2,3-dichlorophenylpiperazine

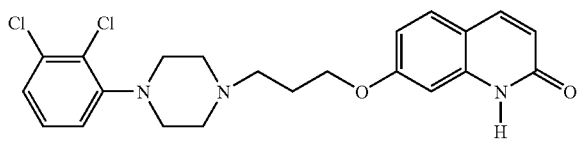 [SMILES: O=c1ccc2ccc(OCCCN3CCN(c4cccc(Cl)c4Cl)CC3)cc2[nH]1]

DM-14857, OPC-14857: 7-{4-[4-(2,3-dichlorophenyl)-1-piperazinyl]butoxy}-2-(1H)-quinolinone, also called dehydroaripiprazole

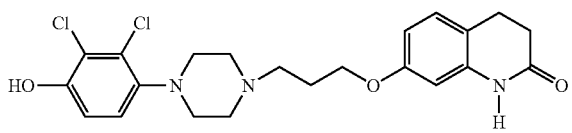 [SMILES: O=C1CCc2ccc(OCCCN3CCN(c4ccc(O)c(Cl)c4Cl)CC3)cc2N1]

DM-1451: 7-{4-[4-(2,3-dichloro-4-hydroxyphenyl)-1-piperazinyl]butoxy}-3,4-dihydro-2-(1H)-quinolinone, and hydroxyaripiprazole

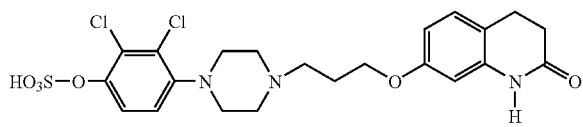 [SMILES: O=C1CCc2ccc(OCCCN3CCN(c4ccc(OS(=O)(=O)O)c(Cl)c4Cl)CC3)cc2N1]

DM-1458: 2,3-dichloro-4-{4-[4-(2-oxo-1,2,3,4-tetrahydroquinolin-7-yloxy)-butyl]-piperazin-1-yl}-phenyl sulfate, and sulfated hydroxyaripiprazole

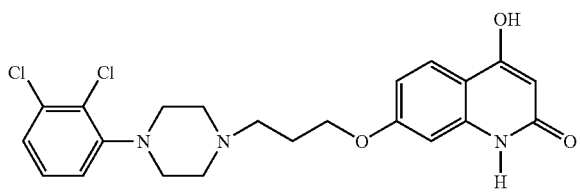 [SMILES: O=c1cc(O)c2ccc(OCCCN3CCN(c4cccc(Cl)c4Cl)CC3)cc2[nH]1]

DM-1452: 7-{4-[4-(2,3-dichlorophenyl)-1-piperazinyl]butoxy}-3,4-dihydro-4-hydroxy-2-(1H)-quinolinone, and benzyl hydroxyaripiprazole

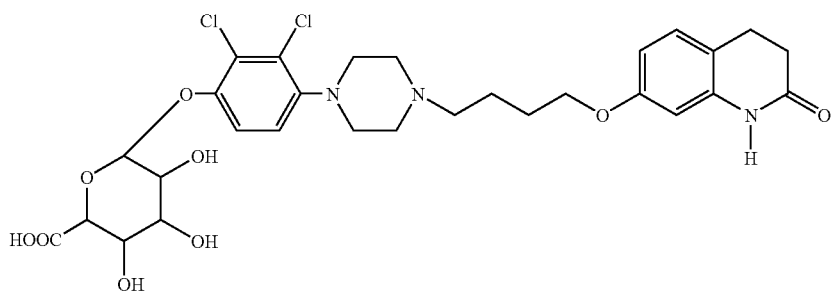 [SMILES: O=C1CCc2ccc(OCCCCN3CCN(c4ccc(OC5OC(C(=O)O)C(O)C(O)C5O)c(Cl)c4Cl)CC3)cc2N1]

DM-1454: DM-1454 is the glucuronide of DM-1451. This structure is also know by the following names:
1β-(2,3-dichloro-4-{4-[4-(2-oxo-1,2,3,4-tetrahydroquinolin-7-yloxy)-butyl]piperazin-1-yl}-phenoxy)-D-glucopyaranuronic acid,
1β-(2,3-dichloro-4-{4-[4-(2-oxo-1,2,3,4-tetrahydroquinolin-7-yloxy)-butyl]-piperazin-1-yl}-phenyl-beta)-D-glucopyaranosiduronic acid,
1β-(2,3-dichloro-4-{4-[4-(2-oxo-1,2,3,4-tetrahydroquinolin-7-yloxy)-butyl]-piperazin-1-yl}-phenyl)-beta)-D-Glucuronide,
1β-(2,3-dichloro-4-{4-[4-(2-oxo-1,2,3,4-tetrahydroquinolin-7-yloxy)-butyl]-piperazin-1-yl}-phenyl-beta)-D-glucuronic acid, and glucuronide aripiprazole.

All of the aforementioned carbostyril derivatives may be used as a first component in the practice of the present invention.

Aripiprazole, also called 7-{4-[4-(2,3-dichlorophenyl)-1-piperazinyl]butoxy}-3,4-dihydro-2(1H)-quinolinone, is a carbostyril compound useful as the effective ingredient for treating schizophrenia (JP-A-2-191256, U.S. Pat. No. 5,006,528). Aripiprazole is also known as 7-[4-[4-(2,3-dichlorophenyl)-1-piperazinyl]butoxy]-3,4-dihydrocarbostyril, Abilify, OPC-14597, OPC-31 and BMS-337039. Aripiprazole possesses 5-HT$_{1A}$ receptor agonist activity, and is known as a useful compound for treating types of depression and refractory depression, such as endogenous depression, major depression, melancholia and the like (WO 02/060423A2; Jordan et al. U.S. Patent Application 2002/0173513A1). Aripiprazole has activity as an agonist at serotonin receptors and dopamine receptors, and acts as an agonist or partial agonist at the serotonin 5HT$_{1A}$ receptor and as an agonist or partial agonist at the dopamine D$_2$ receptor.

Aripiprazole is an antipsychotic drug having new mechanism of action which is different from that of other atypical antipsychotic drugs. The available typical and atypical antipsychotic drugs act as antagonists at the dopamine-D$_2$ receptors. In contrast, aripiprazole acts as a partial agonist at the dopamine D$_2$ receptor (Ishigooka Jyunya and Inada Ken: RINSHO SEISHIN YAKURI, Vol. 4, pp 1653-1664, (2001); Burris, K. D. et al.: J. Pharmacol. Exp. Ther., 302, pp 381-389, (2002)). In addition to the partial agonist action at dopamine-D$_2$ receptors, aripiprazole has activity as a partial agonist at the serotonin 5-HT$_{1A}$ receptor, as well as antagonist action serotonin 5-HT$_{2A}$ receptors. Accordingly, aripiprazole is a drug belonging to new category defined as a dopamine-serotonin system stabilizer (dopamine-serotonin nervous system stabilizer (Burris, K. D. et al., J. Pharmacol. Exp. Ther., 302, pp 381-389, 2002; Jordan, S. et al., Eur. J. Pharmacol. 441, pp 137-140, 2002).

Methods of Preparing Aripiprazole

Aripiprazole and aripiprazole metabolites to be used in the present invention may be any of form, for example, free bases, polymorphisms of every type of crystal, hydrate, salt (acid addition salts, etc.) and the like. Among of these forms, anhydrous aripiprazole crystals B is a preferred form.

As to method for preparing the anhydrous aripiprazole crystals B, for example it is prepared by heating aripiprazole hydrate A as follows.

Aripiprazole Hydrate A

Figure 1:
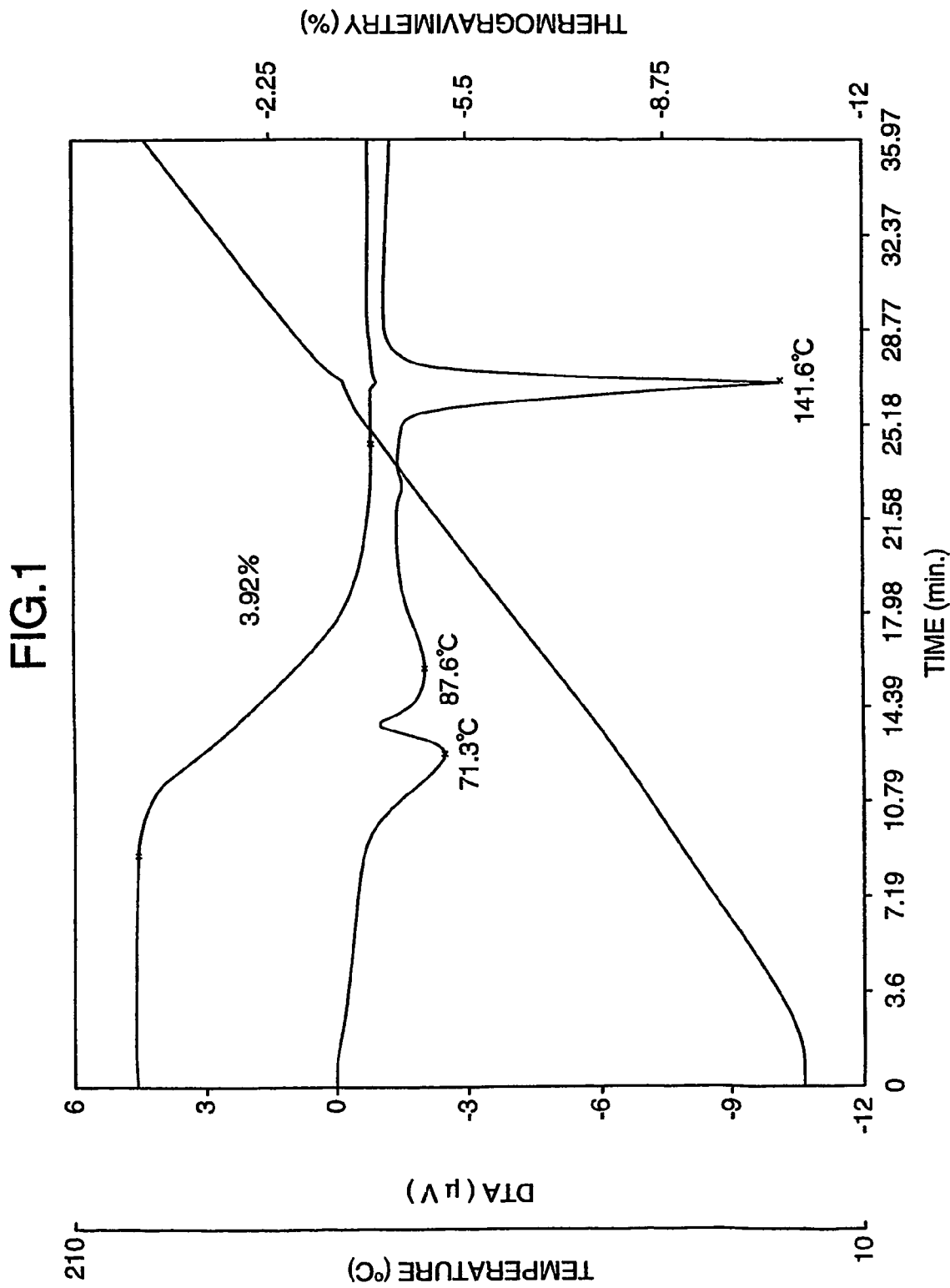
FIG. 1 is the thermogravimetric/differential thermogram of the aripiprazole hydrate A obtained in Reference Example 4.

The aripiprazole hydrate A having the physicochemical properties shown in (1)-(5) as follows:

(1) It has an endothermic curve which is substantially identical to the thermogravimetric/differential thermal analysis (heating rate 5° C./min) endothermic curve shown in FIG. 1. Specifically, it is characterized by the appearance of a small peak at about 71° C. and a gradual endothermic peak around 60° C. to 120° C.

Figure 2:
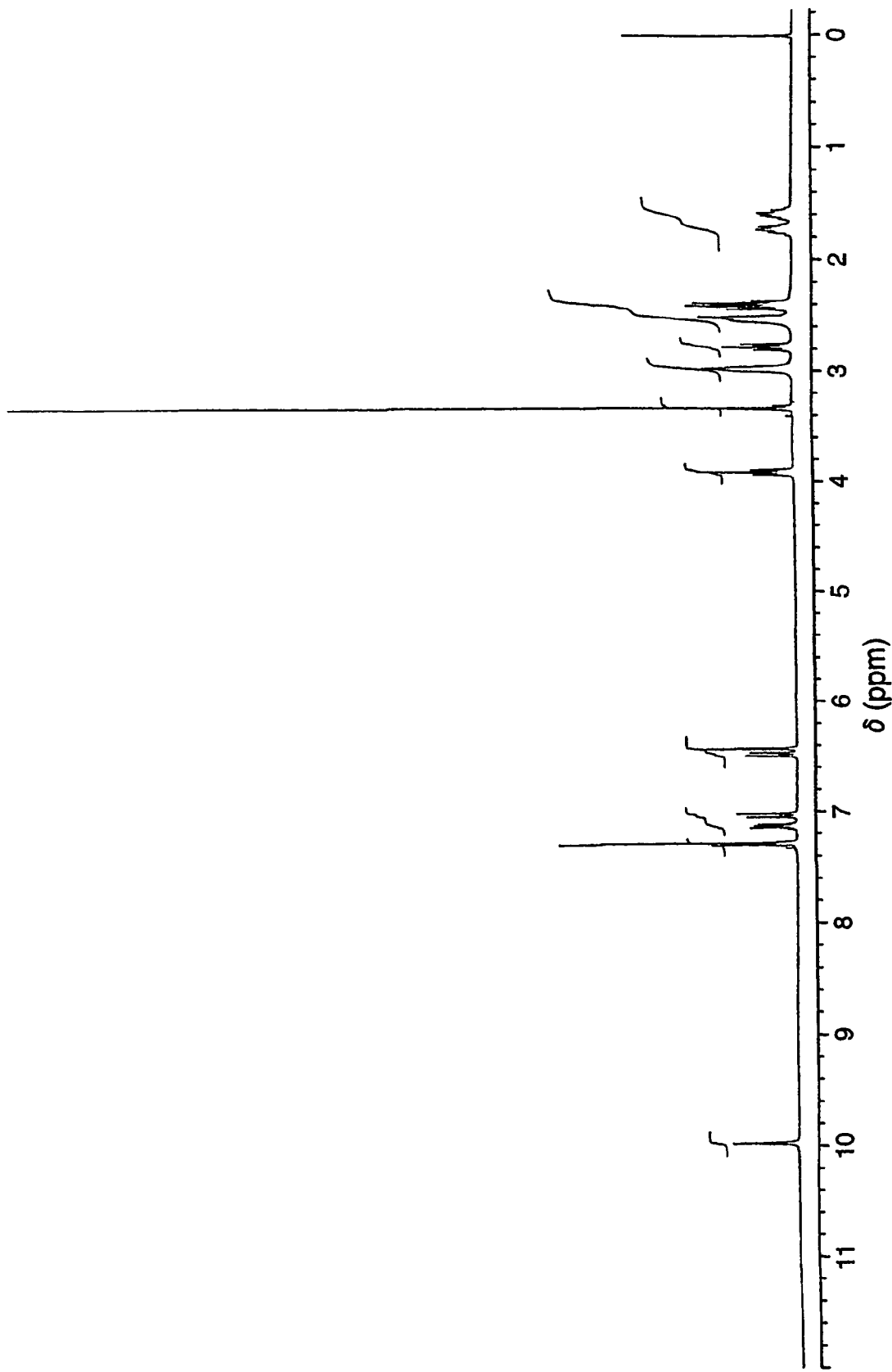
FIG. 2 is the $^1$H-NMR spectrum (DMSO-d$_6$, TMS) of the aripiprazole hydrate A obtained in Reference Example 4.

(2) It has an $^1$H-NMR spectrum which is substantially identical to the $^1$H-NMR spectrum (DMSO-$d_6$, TMS) shown in FIG. 2. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

Figure 3:
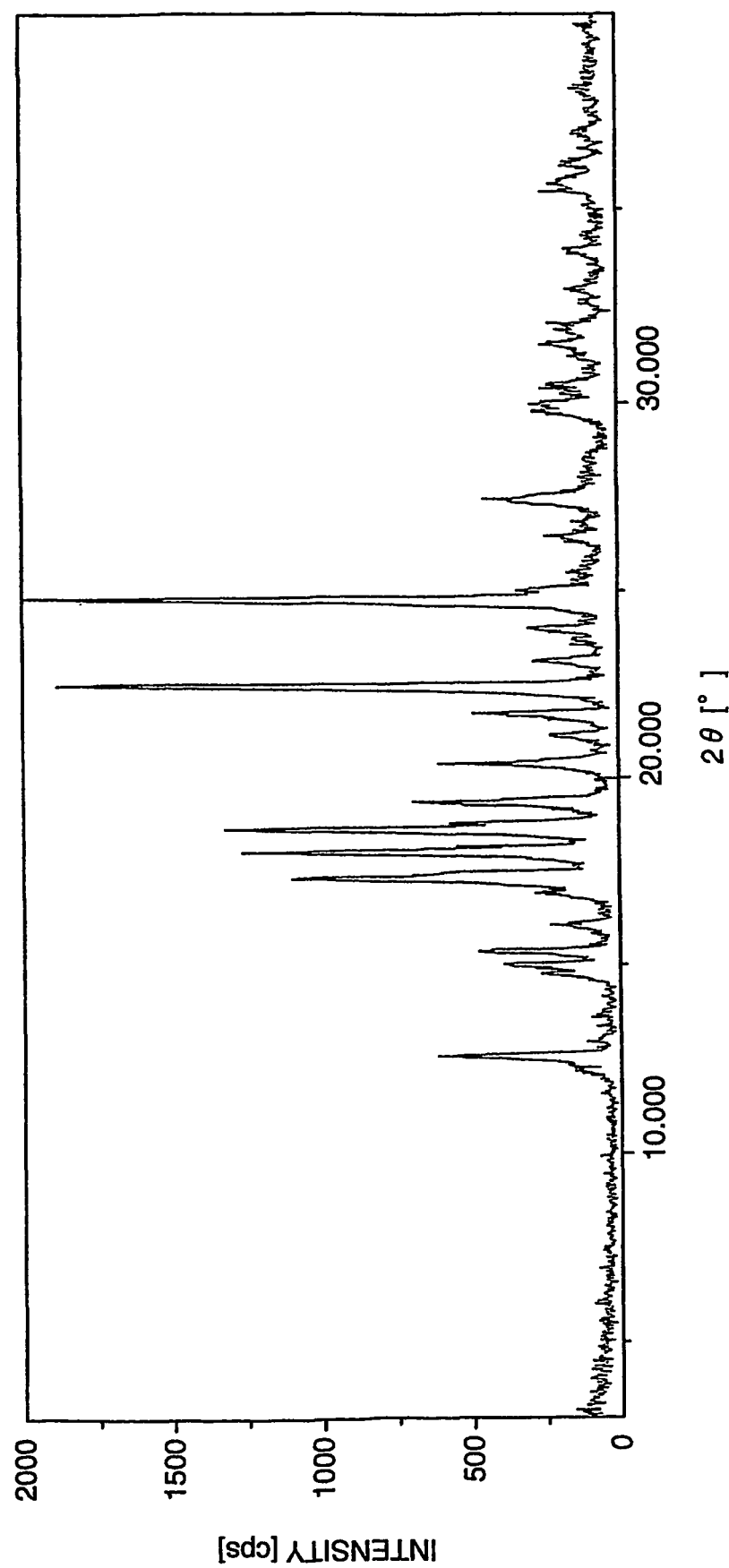
FIG. 3 is the powder X-ray diffraction diagram of the aripiprazole hydrate A obtained in Reference Example 4.

(3) It has a powder x-ray diffraction spectrum which is substantially identical to the powder x-ray diffraction spectrum shown in FIG. 3. Specifically, it has characteristic peaks at 2θ=12.6°, 15.4°, 17.3°, 18.0°, 18.6°, 22.5° and 24.8°.

(4) It has clear infrared absorption bands at 2951, 2822, 1692, 1577, 1447, 1378, 1187, 963 and 784 cm$^{-1}$ on the IR (KBr) spectrum.

(5) It has a mean particle size of 50 μm or less.

Method for Preparing Aripiprazole Hydrate A

Aripiprazole hydrate A is prepared by milling conventional aripiprazole hydrate. Conventional milling methods can be used to mill conventional aripiprazole hydrate. For example, conventional aripiprazole hydrate can be milled in a milling machine. A widely used milling machine such as an atomizer, pin mill, jet mill or ball mill can be used. Among of these, the atomizer is preferably used.

Regarding the specific milling conditions when using an atomizer, a rotational speed of 5000-15000 rpm could be used for the main axis, for example, with a feed rotation of 10-30 rpm and a screen hole size of 1-5 mm.

The mean particle size of the aripiprazole hydrate A obtained by milling may be normally 50 μm or less, preferably 30 μm or less. Mean particle size can be ascertained by the particle size measuring method described hereinafter.

Anhydrous Aripiprazole Crystals B

Anhydrous Aripiprazole crystals B of the present invention have the physicochemical properties given in (6)-(10) below.

Figure 4:
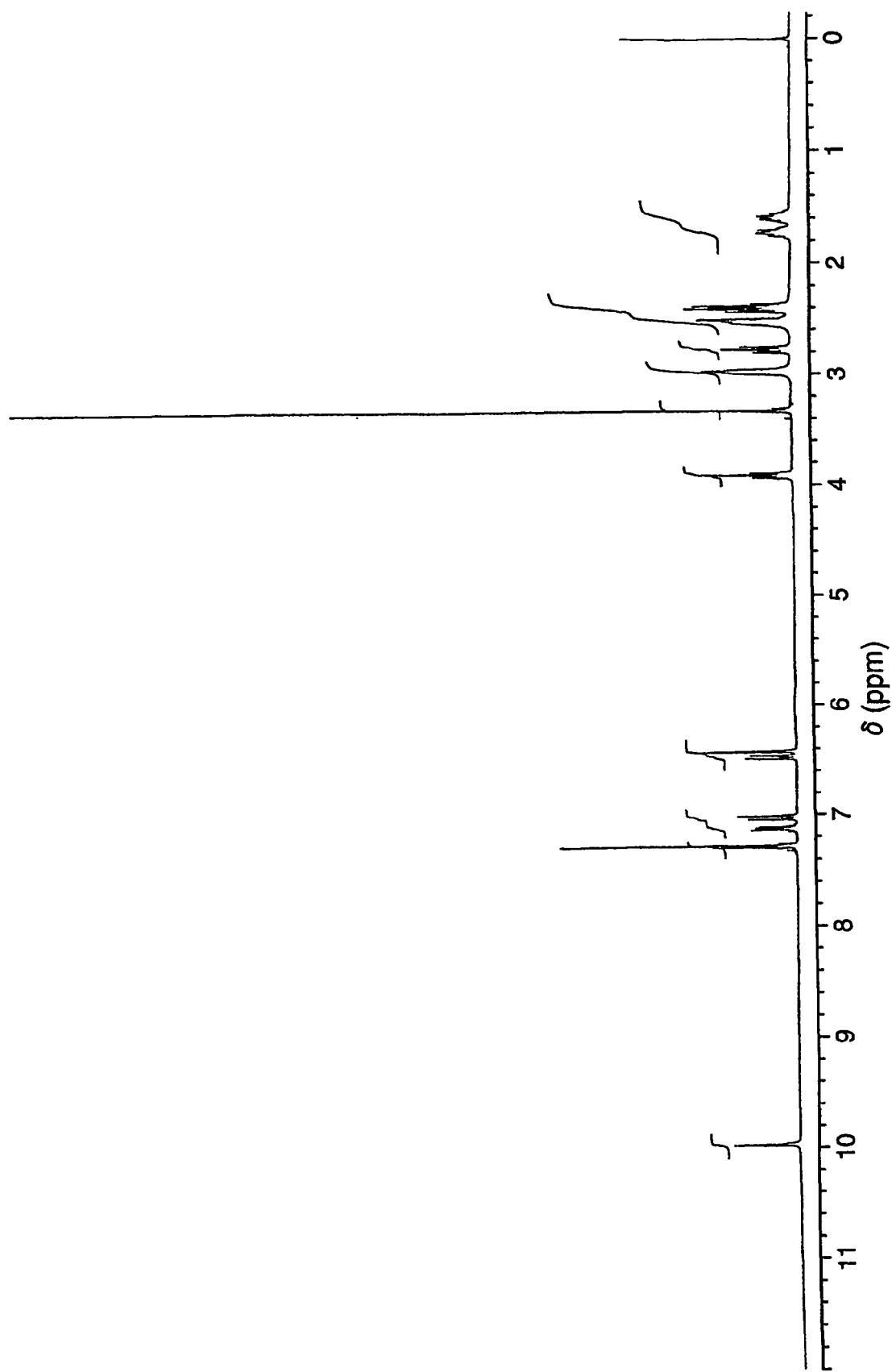
FIG. 4 is the $^1$H-NMR spectrum (DMSO-d$_6$, TMS) of the anhydrous aripiprazole crystals B obtained in Example 1.

(6) They have an $^1$H-NMR spectrum which is substantially identical to the $^1$H-NMR spectrum (DMSO-$d_6$, TMS) shown in FIG. 4. Specifically, they have characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

Figure 5:
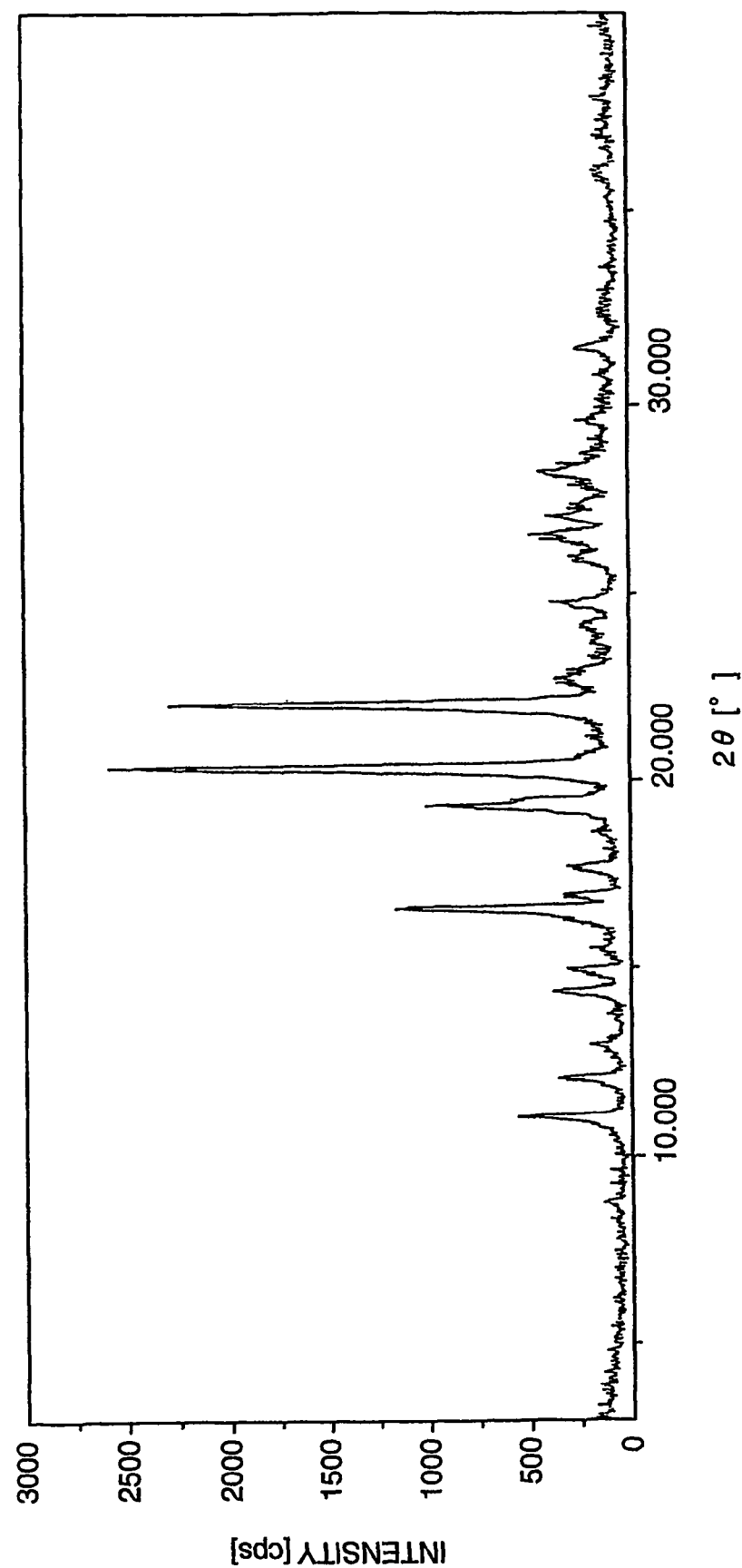
FIG. 5 is the powder X-ray diffraction diagram of the anhydrous aripiprazole crystals B obtained in Example 1.

(7) They have a powder x-ray diffraction spectrum which is substantially identical to the powder x-ray diffraction spectrum shown in FIG. 5. Specifically, they have characteristic peaks at 2θ=11.0°, 16.6°, 19.3°, 20.3° and 22.1°.

(8) They have clear infrared absorption bands at 2945, 2812, 1678, 1627, 1448, 1377, 1173, 960 and 779 cm$^{-1}$ on the IR (KBr) spectrum.

(9) They exhibit an endothermic peak near about 141.5° C. in thermogravimetric/differential thermal analysis (heating rate 5° C./min).

(10) They exhibit an endothermic peak near about 140.7° C. in differential scanning calorimetry (heating rate 5° C./min).

When the small particle size is required for solid preparation, such as tablets and other solid dose formulations including for example flash melt formulations, the mean particle size is preferably 50 μm or less.

Method for Preparing Anhydrous Aripiprazole Crystals B

The anhydrous aripiprazole crystals B of the present invention are prepared, for example, by heating the aforementioned aripiprazole hydrate A at 90-125° C. The heating time is generally about 3-50 hours, but cannot be stated unconditionally, because it differs depending on heating temperature. The heating time and heating temperature are inversely related, so that for example when the heating time is longer, then the heating temperature is lower, and when the heating temperature is higher then the heating time is shorter. Specifically, if the heating temperature of aripiprazole hydrate A is 100° C., the heating time may be 18 hours or more, or preferably about 24 hours. If the heating temperature of aripiprazole hydrate A is 120° C., on the other hand, the heating time may be about 3 hours. The anhydrous aripiprazole crystals B of the present invention can be prepared with certainty by heating aripiprazole hydrate A for about 18 hours at 100° C., and then heating it for about 3 hours at 120° C. The anhydrous aripiprazole crystals B of the present invention can also be obtained if the heating time is extended still further, but this method may not be economical.

When small particle size is not required for the formulation, e.g., when drug substance is being prepared for injectable or oral solution formulations, anhydrous aripiprazole crystals B can be also obtained by the following process.

Anhydrous aripiprazole crystals B of the present invention are prepared for example by heating conventional anhydrous aripiprazole crystals at 90-125° C. The heating time is generally about 3-50 hours, but cannot be stated unconditionally because it differs depending on heating temperature. The heating time and heating temperature are inversely related, so that for example if the heating time is longer, the heating temperature is lower, and if the heating time is shorter, the heating temperature is higher. Specifically, if the heating temperature of the anhydrous aripiprazole crystals is 100° C., the heating time may be about 4 hours, and if the heating temperature is 120° C. the heating time may be about 3 hours.

Furthermore, anhydrous aripiprazole crystals B of the present invention are prepared for example, by heating conventional aripiprazole hydrate at 90-125° C. The heating time is generally about 3-50 hours, but cannot be stated unconditionally because it differs depending on heating temperature. The heating time and heating temperature are inversely related, so that for example, if the heating time is longer, the heating temperature is lower, and if the heating time is shorter, the heating temperature is higher. Specifically, if the heating temperature of the aripiprazole hydrate is 100° C., the heating time may be about 24 hours, and if the heating temperature is 120° C. the heating time may be about 3 hours.

The anhydrous aripiprazole crystals which are the raw material for preparing the anhydrous aripiprazole crystals B of the present invention are prepared for example by Method A or B below.

Method A: Process for Preparing Crude Crystals of Aripiprazole

Conventional anhydrous aripiprazole crystals are prepared by well-known methods, as described in Example 1 of Japanese Unexamined Patent Publication No. 191256/1990. 7-(4-bromobutoxy)-3,4-dihydrocarbostyril, is reacted with 1-(2,3-dichlorophenyl)piperazine and the thus obtained crude aripiprazole crystals are re-crystallized from ethanol.

Method B: Process for Preparing Conventional Anhydrous Aripiprazole

The Method B is described in the Proceedings of the 4th Joint Japanese-Korean Symposium on Separation Technology (Oct. 6-8, 1996). The aripiprazole hydrate which is the raw material for preparing the anhydrous aripiprazole crystals B of the present invention is prepared for example by Method C below.

Method C: Method for Preparing Conventional Aripiprazole Hydrate

Aripiprazole hydrate is easily obtained by dissolving the anhydrous aripiprazole crystals obtained by Method A above in a hydrous solvent, and heating and then cooling the resulting solution. Using this method, aripiprazole hydrate is precipitated as crystals in the hydrous solvent.

An organic solvent containing water is usually used as the hydrous solvent. The organic solvent may be preferable one which is miscible with water, for example an alcohol such as methanol, ethanol, propanol or isopropanol, a ketone such as acetone, an ether such as tetrahydrofuran, dimethylformamide, or a mixture thereof, ethanol is particularly desirable. The amount of water in the hydrous solvent may be 10-25% by volume of the solvent, or preferably close to 20% by volume.

Aripiprazole can easily form an acid addition salt with a pharmaceutically acceptable acid. As to such acid, for example, an inorganic acid, such as sulfuric acid, nitric acid, hydrochloric acid, phosphoric acid, hydrobromic acid, etc.; an organic acid such as, acetic acid, p-toluenesulfonic acid, methanesulfonic acid, oxalic acid, maleic acid, fumaric acid, malic acid, tartaric acid, citric acid, benzoic acid, etc. can be exemplified. Similar to aripiprazole of free forms, these acid addition salts can also be used as the active ingredient compounds in the present invention.

The objective compound thus obtained through each one of production steps, is separated from the reaction system by usual separation means, and can be further purified. As to the separation and purification means, for example, distillation method, solvent extraction method, dilution method, re-crystallization method, column chromatography, ion-exchange chromatography, gel chromatography, affinity chromatography, preparative thin-layer chromatography and the like can be exemplified.

The Pharmaceutical Composition: the Second Ingredient

In the composition of the present invention, a mood stabilizer is used as the second ingredient. Compounds which function as mood stabilizers can be widely used as the mood stabilizers and are known to one of ordinary skill in the art.

A non-limiting list of mood stabilizers which may be used in the present invention includes, lithium, valproic acid, divalproex sodium, carbamazepine, oxcarbamazepine, zonisamide, lamotragine, topiramate, gabapentin, levetiracetam and clonazepam.

The mood stabilizer may be either in the form of a free base or a salt (an acid addition salt or the like). Further, the mood stabilizer may be either a racemic modifications or R and S enantiomers. The mood stabilizers may be either a single use of one mood stabilizer, and in case of need, two or more of the mood stabilizers may be used in combination. Use of one mood stabilizer is preferred.

The mood stabilizer can easily form an acid addition salt with a pharmaceutically acceptable acid. As to such acid, for example, an inorganic acid, such as sulfuric acid, nitric acid, hydrochloric acid, phosphoric acid, hydrobromic acid, etc.; an organic acid such as, acetic acid, p-toluenesulfonic acid, methanesulfonic acid, oxalic acid, maleic acid, fumaric acid, malic acid, tartaric acid, citric acid, benzoic acid, etc. can be exemplified. Similar to the reuptake inhibitor of free forms, these acid addition salts can also be used as the active ingredient compounds in the present invention.

Among the mood stabilizers, a compound having an acidic group can easily form salt by reacting with a pharmaceutically acceptable basic compound. As to such basic compound, a metal hydroxide, for example, sodium hydroxide, potassium hydroxide, lithium hydroxide, calcium hydroxide and the like; an alkali metal carbonate or bicarbonate, for example sodium carbonate, potassium carbonate, sodium hydrogencarbonate, potassium hydrogencarbonate and the like; a metal alcoholate, for example sodium methylate, potassium ethylate and the like can be exemplified.

The thus obtained salt form of mood stabilizer is separated from the reaction system by usual separation means, and can be further purified. As to the separation and purification means, for example, distillation method, solvent extraction method, dilution method, recrystallization method, column chromatography, ion-exchange chromatography, gel chromatography, affinity chromatography, preparative thin-layer chromatography and the like can be exemplified.

Combination of the First Ingredient with the Second Ingredient

As to pharmaceutical compositions comprising a combination of carbostyril derivatives with activity as dopamine-serotonin stabilizers, and mood stabilizers, non-limiting examples of aripiprazole and dehydroaripiprazole are described herein. It is to be understood that the present invention also comprises a combination of carbostyril derivatives with activity as dopamine-serotonin stabilizers, and mood stabilizers, wherein the carbostyril derivatives are other metabolites of aripiprazole described herein.

When aripiprazole is combined with at least one mood stabilizer, the following are non-limiting examples of such combinations: aripiprazole/lithium, aripiprazole/valproic acid, aripiprazole/divalproex sodium, aripiprazole/carbamazapine, aripiprazole/oxcarbamazapine, aripiprazole/zonisamide, aripiprazole/lamotragine, aripiprazole/topiramate, aripiprazole/gabapentin, aripiprazole/levetiracetam and aripiprazole/clonazepam. Among these combinations, the following are particularly preferable: aripiprazole/carbamazapine, aripiprazole/oxcarbamazapine, aripiprazole/zonisamide, aripiprazole/lamotragine, aripiprazole/topiramate, aripiprazole/gabapentin, aripiprazole/levetiracetam and aripiprazole/clonazepam. The pharmaceutical composition comprising the above preferable combination possesses excellent efficacy. Therefore such composition has fewer side-effects and an excellent safety profile.

In another embodiment of the present invention, aripiprazole, or a metabolite thereof may be combined with more than one mood stabilizer. Metabolites of aripiprazole that may be used in the present invention include, but are not limited to, OPC-14857, DM-1458, DM-1451, DM-1452, DM-1454 and DCPP as shown in FIG. 8. Any one of these metabolites may be used in the present invention. The following sentences describe a combination of dehydroaripiprazole with specific mood stabilizers, however it is to be understood that any one of DM-1458, DM-1451, DM-1452, DM-1454 or DCPP, as shown in FIG. 8, could be substituted for dehydroaripiprazole in these disclosed combinations. Dehydroaripiprazole (also called OPC-14857 in FIG. 8) is a preferred metabolite of aripiprazole. As to the combination of dehydroaripiprazole with one or more mood stabilizers, the following are non-limiting examples of such combinations: dehydroaripiprazole/lithium, dehydroaripiprazole/valproic acid, dehydroaripiprazole/divalproex sodium, dehydroaripiprazole/carbamazepine, dehydroaripiprazole/oxcarbamazepine, dehydroaripiprazole/zonisamide, dehydroaripiprazole/lamotragine, dehydroaripiprazole/topiramate, dehydroaripiprazole/gabapentin, dehydroaripiprazole/levetiracetam and dehydroaripiprazole/clonazepam. Among these combinations, the following are particularly preferable: dehydroaripiprazole/carbamazepine, dehydroaripiprazole/oxcarbamazapine, dehydroaripiprazole/zonisamide, dehydroaripiprazole/lamotragine, dehydroaripiprazole/topiramate, dehydroaripiprazole/gabapentin, dehydroaripiprazole/levetiracetam and dehydroaripiprazole/clonazepam. The pharmacuetical composition comprising the above preferable combination possesses excellent efficacy. Therefore such composition has fewer side-effects and an excellent safety profile.

Method of Treating a Mood Disorder, Especially Bipolar Disorder or Mania

Patients with mood disorders may be treated with the compositions of the present invention. Such mood disorders include but are not limited to bipolar disorder, bipolar disorder I, bipolar disorder II, bipolar disorder with and without psychotic features, mania, acute mania, bipolar depression or mixed episodes. Preferred disorders treated with the method and compositions of the present invention are bipolar disorder and mania. Treatment comprises administration of the compositions of the present invention to a patient with a mood disorder such as bipolar disorder or mania, with or without psychotic features, in an amount and dose regimen effective to treat the mood disorder. The present invention includes treatment of mood disorders wherein both the carbostyril derivative with the previously stated activity and the mood stabilizer are combined together with a pharmaceutically acceptable carrier in a composition. The present invention further includes treatment of mood disorders wherein both the carbostyril derivative with the previously stated activity is combined with a pharmaceutically acceptable carrier in one composition, the mood stabilizer is combined with a pharmaceutically acceptable carrier in a second composition, and the two compositions are administered at the same or different times to provide the desired treatment.

Dosage

Dosage of the drug used in the present invention is decided by considering the properties of each constituting drug to be combined, the properties of drugs after combination and symptoms of the patient. As stated above, the carbostyril derivatives and mood stabilizers may be administered separately and not combined in one composition. General outlines of the dosage are provided in the following guidelines.

Aripiprazole or a metabolite, such as dehydroaripiprazole, DM-1458, DM-1451, DM-1452, DM-1454 or DCPP: generally about 0.1 to about 100 mg/once a day (or about 0.05 to about 50 mg/twice a day), preferably about 1 to about 30 mg/once a day (or about 0.5 to about 15 mg/twice a day).

The aripiprazole, or metabolite thereof, may be combined with at least one of any of the following mood stabilizers at the dose ranges indicated, or administered separately:

Lithium: generally about 300 to about 2400 mg/day, 300 mg to 1200 mg twice per day, preferably until the plasma lithium concentration is about 0.8-1.2 mmol/L.

Valproic acid: generally about 750 mg to 2000 mg/day, or 10 to 20 mg/kg/day.

Divalproex sodium: generally about 500 to 2500 mg/day.

Carbamazepine: generally about 100 to 1000 mg/day, preferably until plasma levels reach between about 6.0 to 9.0 mg/L.

Oxcarbamazepine: generally about 600 to 2100 mg/day.

Zonisamide: generally about 100 to 500 mg/day.

Lamotragine: generally about 50 to 500 mg/day, preferably 100 to 400 mg/day.

Topiramate: generally, about 25 to about 500 mg/day.

Gabapentin: generally, about 600 to 2400 mg/once a day.

Levetiracetam: generally, about 250 to about 3000 mg/day.

Clonazepam: generally, about 0.1 to 60 mg/day.

Generally, the weight ratio of the first ingredient to the second ingredient is selected in accordance with the above-mentioned guideline. As to the ratio of the first ingredient and the second ingredient, if the first ingredient is about 1 part by weight of the former, the second ingredient is used at about 0.01 to about 500 parts by weight, preferably about 0.1 to about 100 parts by weight.

Pharmaceutically Acceptable Carriers

Pharmaceutically acceptable carriers include diluents and excipients generally used in pharmaceutical preparations, such as fillers, extenders, binders, moisturizers, disintegrators, surfactant, and lubricants.

The pharmaceutical composition of the present invention may be formulated as an ordinary pharmaceutical preparation, for example in the form of tablets, flash melt tablets, pills, powder, liquid, suspension, emulsion, granules, capsules, suppositories or injection (liquid, suspension, etc.), troches, intranasal spray percutaneous patch and the like.

In case of shaping to tablet formulation, a wide variety of carriers that are known in this field can be used. Examples include lactose, saccharose, sodium chloride, glucose, urea, starch, xylitol, mannitol, erythritol, sorbitol, calcium carbonate, kaolin, crystalline cellulose, silic acid and other excipients; water, ethanol, propanol, simple syrup, glucose solution, starch solution, gelatin solution, carboxymethyl cellulose, shellac, methyl cellulose, potassium phosphate, polyvinyl pyrrolidone and other binders; dried starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch, lactose and other disintegrators; white sugar, stearin, cacao butter, hydrogenated oil and other disintegration inhibitors; quaternary ammonium salt, sodium lauryl sulfate and other absorption accelerator; glycerine, starch and other moisture retainers; starch, lactose, kaolin, bentonite, colloidal silic acid and other adsorbents; and refined talc, stearate, boric acid powder, polyethylene glycol and other lubricants and the like. Tablets can also be formulated if necessary as tablets with ordinary coatings, such as sugar-coated tablets, gelatin-coated tablets, enteric coated tablets and film coated tablets, as well as double tablets and multilayered tablets.

In case of shaping to pills, a wide variety of carriers that are known in this field can be used. Examples include glucose, lactose, starch, cacao butter, hardened vegetable oil, kaolin, talc and other excipients; gum arabic powder, traganth powder, gelatin, ethanol and other binders; and laminaran, agar and other disintegrators and the like.

In case of shaping to a suppository formulation, a wide variety of carriers that are known in the field can be used. Examples include polyethylene glycol, cacao butter, higher alcohol, esters of higher alcohol, gelatin semi-synthetic glyceride and the like.

Capsules are prepared according to ordinary methods by mixing anhydrous aripiprazole crystals as the first ingredient and the second ingredient, and the various carriers described above and packing them in hard gelatin capsules, soft capsules hydroxypropylmethyl cellulose capsules (HPMC capsules) and the like.

In addition, colorants, preservatives, perfumes, flavorings, sweeteners and the like as well as other drugs may be contained in the pharmaceutical composition.

The amounts of the first ingredient and the second ingredient to be contained in the pharmaceutical composition of the present invention are suitably selected from a wide range depending on the diseases to be treated. Generally, about 1 to 70 parts by weight, preferably about 1 to 30 parts by weight of the first ingredient and the second ingredient are combined in the total amount on the basis of the pharmaceutical composition.

The methods for administration of the pharmaceutical composition of the present invention are not specifically restricted. The composition is administered depending on each type of preparation form, and the age, gender and other condition of the patient (degree and conditions of the disease, etc.). For example, tablets, pills, liquids, suspensions, emulsions, granules and capsules are administered orally. In case of injection preparation, it is administered intravenously either singly or mixed with a common auxiliary liquid such as solutions of glucose or amino acid. Further, if necessary, the injection preparation is singly administered intradermally, subcutaneously or intraperitoneally. In case of a suppository, it is administered intrarectally.

Administration forms of the pharmaceutical composition of the present invention may be any type by which the effective levels of both aripiprazole and mood stabilizers can be provided in vivo at the same time. In one embodiment, aripiprazole together with a mood stabilizer are contained in one pharmaceutical composition and this composition may be administered. On the other hand, each one of aripiprazole and a mood stabilizer are contained individually in a pharmaceutical preparation respectively, and each one of these preparations may be administered at the same or at different times.

Dosage of the pharmaceutical composition of the present invention for treating and improving mood disorders may be used relatively in a small amount, because the composition possesses excellent efficacy. Therefore the composition has fewer side-effects and an excellent safety profile.

The pharmaceutical composition of the present invention can be manifest in a wide range of neurotransmission accommodation actions. As a result, the composition of the present invention establishes pseudo-homeostatic dopaminergic and serotoninergic neurotransmission (as a result of partial agonism), which, as a result of neuropathophysiological processes has ceased to function normally. The mood disorders which can be treated by the pharmaceutical composition of the present invention includes the mood disorders classified in "Diagnostic and Statistical Manual of Mental Disorders" Fourth Edition (DSM-IV) published by the American Psychiatric Association. These mood disorders include, for example, bipolar disorder such as bipolar disorder I or II, bipolar disorder with or without psychotic features, mania, acute mania, bipolar depression or mixed episodes.

In addition, the pharrmaceutical composition of the present invention is effective on schizophrenia and other psychotic disorders. These disorders include, for example, depressive disorders such as major depressive disorder, endogenous depression, melancholia, depression in combination with psychotic episodes, refractory depression, dementia of the Alzheimer's disease with depressive symptoms, Parkinson's disease with depressive symptoms, senile dementia, mood disorder associated with cerebral blood vessels, mood disorder following head injury and the like; anxiety disorders such as panic disorder, obsessive-compulsive disorder, generalized anxiety disorder, posttraumatic stress disorder, social phobia, specific phobia and the like; eating disorders; sleep disorders; adjustment disorders; personality disorders; mental retardations; learning disorders; pervasive developmental disorders; attention-deficit and disruptive behavior disorders; tic disorders; delirium; dementia; amnestic disorders; other cognitive disorders; alcohol-related disorders; amphetamine-related disorders; cocaine-related disorders; nicotine-related disorders; sedative-, hypnotic-, or anxiolytic-related disorders; sexual and gender identity disorders. These disorders are classified in "Diagnostic and Statistical Manual of Mental Disorders" Fourth Edition (DSM-IV) published by the American Psychiatric Association.

The present invention will be explained more in detail by illustrating Reference Examples, Example and Formulation Sample Examples. First, analytical methods are explained.

Analytical Methods (1) The $^1$H-NMR spectrum was measured in DMSO-$d_6$ by using TMS as the standard.

(2) Powder X-ray Diffraction

By using RAD-2B diffraction meter manufactured by Rigaku Denki, the powder x-ray diffraction pattern was measured at room temperature by using a Cu Ka filled tube (35 kV 20 mA) as the x-ray source with a wide-angle goniometer, a 1° scattering slit, an 0.15 mm light-intercepting slit, a graphite secondary monochromator and a scintillation counter. Data collection was done in 2θ continuous scan mode at a scan speed of 5°/minute in scan steps of 0.02° in the range of 3° to 40°.

(3) The IR spectrum was measured by the KBr method.

(4) Thermogravimetric/Differential Thermal Analysis

Thermogravimetric/differential thermal analysis was measured by using SSC 5200 control unit and TG/DTA 220 simultaneous differential thermal/thermogravimetric measuring unit manufactured by Seiko Corp. Samples (5-10 mg) were placed in open aluminum pans and heated at from 20° C. to 200° C. in a dry nitrogen atmosphere at a heating rate of 5° C./minute. α-Alumina was used as the standard substance.

(5) Differential Scanning Calorimetry

Thermogravimetric/differential thermal analysis was measured by using SSC 5200 control unit and DSC 220C differential scanning calorimeter manufactured by Seiko Corp. Samples (5-10 mg) were placed in crimped aluminum pans and heated from 20° C. to 200° C. in a dry nitrogen atmosphere at a heating rate of 5° C./minute. α-Alumina was used as the standard substance.

(6) Particle Size Measurement

The particles (0.1 g) to be measured were suspended in a 20 ml n-hexane solution of 0.5 g soy lecithin, and particle size was manufactured by using a size distribution measuring meter (Microtrack HRA, manufactured by Microtrack Co.).

Reference Example 1

7-(4-Chlorobutoxy)-3,4-dihydrocarbostyril (19.4 g) and monohydrochloride 16.2 g of 1-(2,3-dichlorophenyl) piperadine 1 hydrochloride were added to a solution of 8.39 g of potassium carbonate dissolved in 140 ml of water, and refluxed for 3 hours under agitation. After the reaction was complete, the mixture was cooled and the precipitated crystals collected by filtration. These crystals were dissolved in 350 ml of ethyl acetate, and about 210 ml of water/ethyl acetate azeotrope was removed under reflux. The remaining solution was cooled, and the precipitated crystals were collected by filtration. The resulting crystals were dried at 60° C. for 14 hours to obtain 20.4 g (74.2%) of crude product of aripiprazole.

The crude product of aripiprazole (30 g) obtained above was re-crystallized from 450 ml of ethanol according to the methods described in Japanese Unexamined Patent Publication No. 191256/1990, and the resulting crystals were dried at 80° C. for 40 hours to obtain anhydrous aripiprazole crystals. The yield was 29.4 g (98.0%).

The melting point (mp) of these anhydrous aripiprazole crystals was 140° C., which is identical to the melting point of the anhydrous aripiprazole crystals described in Japanese Unexamined Patent Publication No. 191256/1990.

Reference Example 2

The crude product of aripiprazole (6930 g) obtained in Reference Example 1 was heat dissolved by heating in 138 liters of hydrous ethanol (water content 20% by volume) according to the method presented at the 4th Joint Japanese-Korean Symposium on Separation Technology, the solution was gradually (2-3 hours) cooled to room temperature, and then was chilled to near 0° C. The precipitated crystals were collected by filtration, about 7200 g of aripiprazole hydrate (wet-state).

The wet-state aripiprazole hydrate crystals obtained above were dried at 80° C. for 30 hours to obtain 6480 g (93.5%) of aripiprazole hydrate crystals. The melting point (mp) of these crystals was 139.5° C.

The water content of the crystals were confirmed by the Karl Fischer method, the moisture value was 0.03%, thus the crystals were confirmed as anhydrous product.

Reference Example 3

Figure 6:
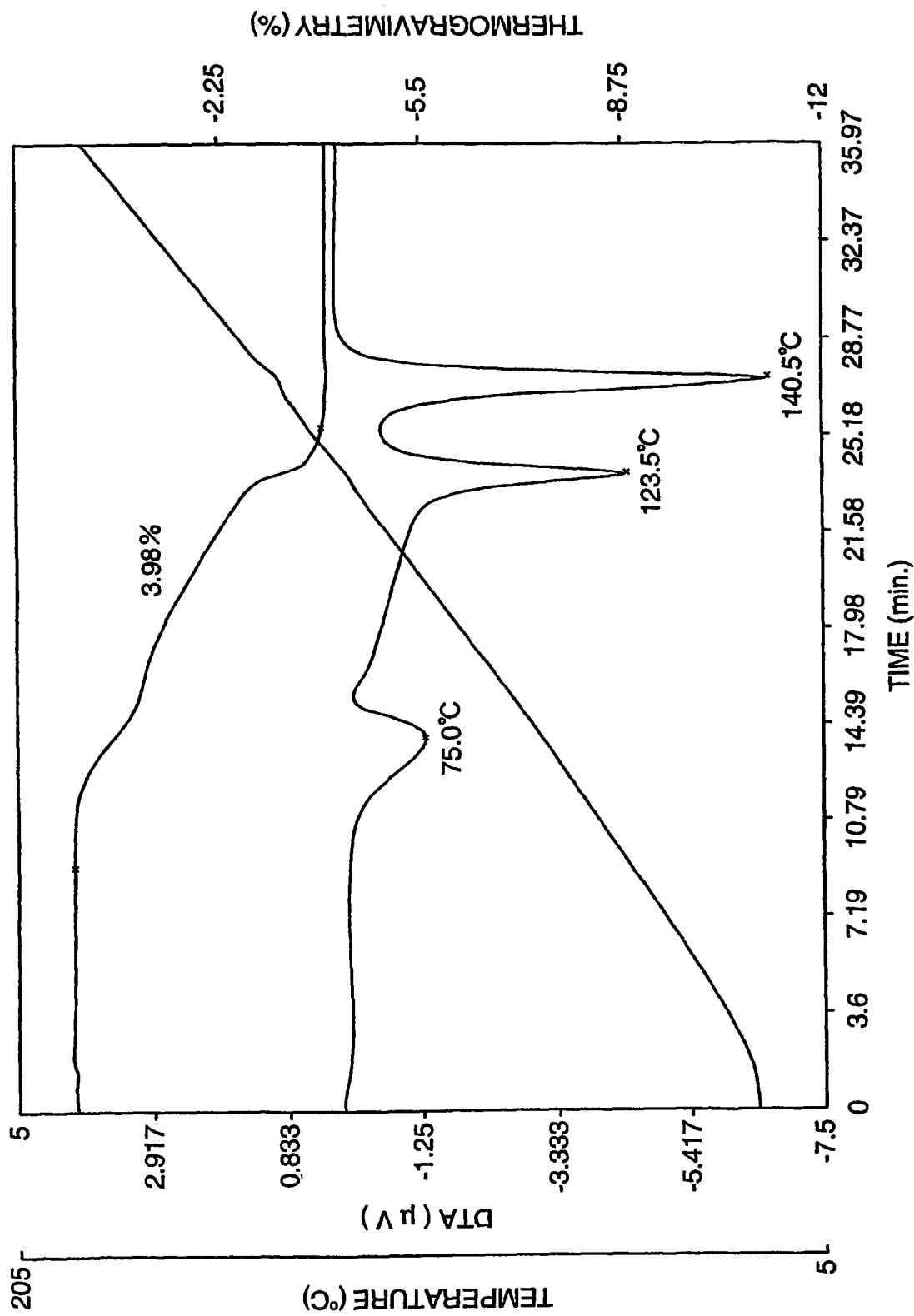
FIG. 6 is the thermogravimetric/differential thermogram of the aripiprazole hydrate obtained in Reference Example 3.

The aripiprazole hydrate (820 g) in wet state obtained from Reference Example 2 was dried at 50° C. for 2 hours to obtain 780 g of aripiprazole hydrate crystals. The moisture value of the crystals had a moisture value was 3.82% measured according to the Karl Fischer method. As shown in FIG. 6, thermogravimetric/differential thermal analysis revealed endothermic peaks at 75.0, 123.5 and 140.5° C. Because dehydration began near at 70° C., there was no clear melting point (mp) was observed.

Figure 7:
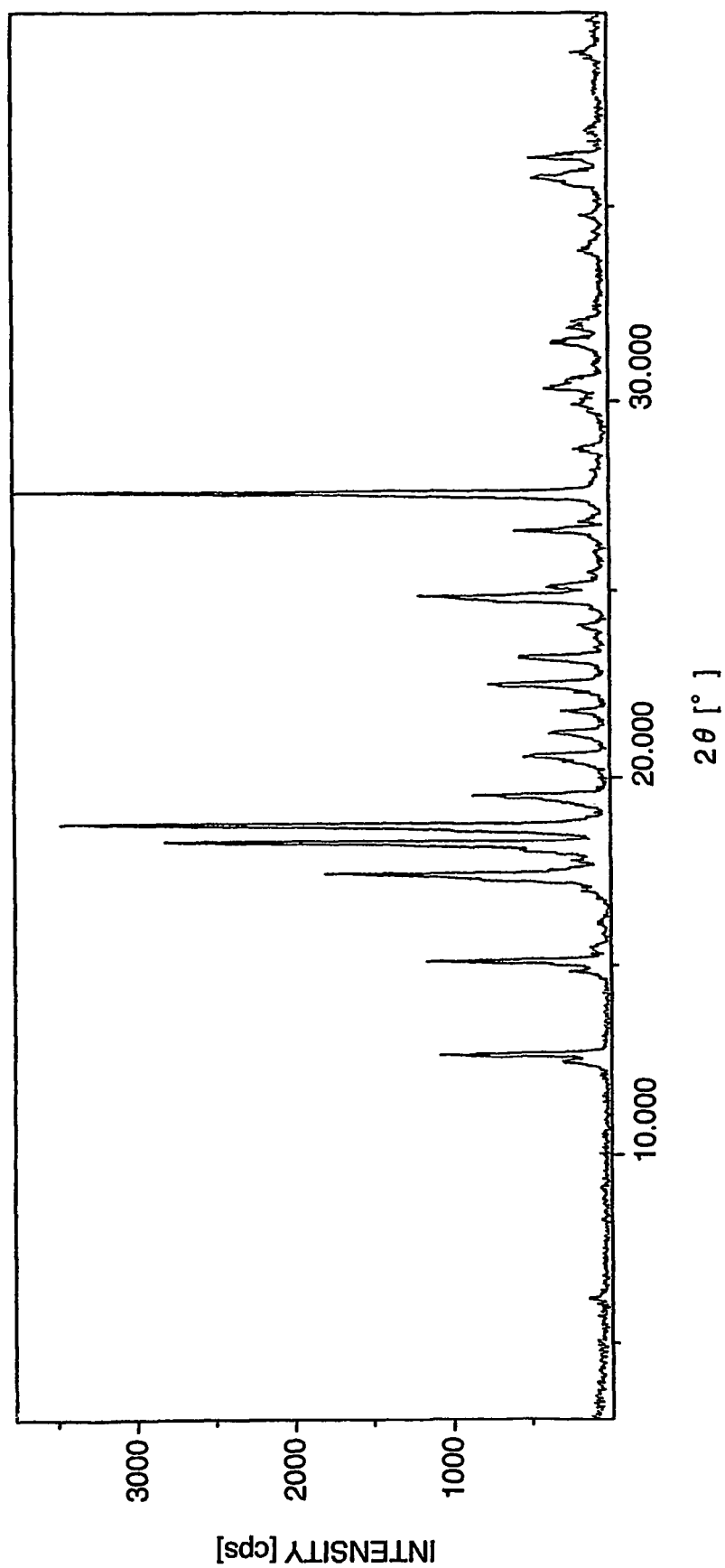
FIG. 7 is the powder X-ray diffraction diagram of aripiprazole hydrate obtained in Reference Example 3.

As shown in FIG. 7, the powder x-ray diffraction spectrum of aripiprazole hydrate obtained by this method exhibited characteristic peaks at 2θ=12.6°, 15.1°, 17.4°, 18.2°, 18.7°, 24.8° and 27.5°.

The powder x-ray diffraction spectrum of this aripiprazole hydrate was identical to the powder x-ray diffraction spectrum of aripiprazole hydrate presented at the 4th Joint Japanese-Korean Symposium on Isolation Technology.

Reference Example 4

The aripiprazole hydrate crystals (500.3 g) obtained in Reference Example 3 were milled by using a sample mill (small size atomizer). The main axis rotation rate was set to 12,000 rpm and the feed rotation rate to 17 rpm, and a 1.0 mm herringbone screen was used. Milling was finished in 3 minutes, and obtained 474.6 g (94.9%) of aripiprazole hydrate A.

The aripiprazole hydrate A (powder) obtained in this way had a mean particle size of 20-25 µm. The melting point (mp) was undetermined because dehydration was observed beginning near at 70° C.

The aripiprazole hydrate A (powder) obtained above exhibited an $^1$H-NMR (DMSO-$d_6$, TMS) spectrum which was substantially identical to the $^1$H-NMR spectrum shown in FIG. 2. Specifically, it had characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

The aripiprazole hydrate A (powder) obtained above had a powder x-ray diffraction spectrum which was substantially identical to the powder x-ray diffraction spectrum shown in FIG. 3. Specifically, it had characteristic peaks at 2θ=12.6°, 15.4°, 17.3°, 18.0°, 18.6°, 22.5° and 24.8°. This pattern is different from the powder x-ray spectrum of unmilled Aripiprazole hydrate shown in FIG. 7.

The aripiprazole hydrate A (powder) obtained above had infrared absorption bands at 2951, 2822, 1692, 1577, 1447, 1378, 1187, 963 and 784 cm$^{-1}$ on the IR (KBr) spectrum.

As shown in FIG. 1, the aripiprazole hydrate A (powder) obtained above had a weak peak at 71.3° C. in thermogravimetric/differential thermal analysis and a broad endothermic peak (weight loss observed corresponding to one molecule of water) between 60-120° C. which was clearly different from the endothermic curve of unmilled aripiprazole hydrate (see FIG. 6).

It will be appreciated that other embodiments and uses will be apparent to those skilled in the art and that the invention is not limited to these specific illustrative examples.

Example 1

The aripiprazole hydrate A (powder) (44.29 kg) obtained in the Reference Examples was dried at 100° C. for 24 hours by using a hot air dryer and further heated at 120° C. for 3 hours, to obtain 42.46 kg (yield; 99.3 %) of anhydrous aripiprazole Crystals B. These anhydrous aripiprazole crystals B had a melting point (mp) of 139.7° C.

The anhydrous aripiprazole crystals B obtained above had an $^1$H-NMR spectrum (DMSO-$d_6$, TMS) which was substantially identical to the $^1$H-NMR spectrum shown in FIG. 4. Specifically, they had characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

The anhydrous aripiprazole crystals B obtained above had a powder x-ray diffraction spectrum which was substantially the identical to the powder x-ray diffraction spectrum shown in FIG. 5. Specifically, they had characteristic peaks at 2θ=11.0°, 16.6°, 19.3°, 20.3° and 22.1°.

The anhydrous aripiprazole crystals B obtained above had remarkable infrared absorption bands at 2945, 2812, 1678, 1627, 1448, 1377, 1173, 960 and 779 cm$^{-1}$ on the IR (KBr) spectrum. The anhydrous aripiprazole crystals B obtained above exhibited an endothermic peak near about at 141.5° C. in thermogravimetric/differential thermal analysis. The anhydrous aripiprazole crystals B obtained above exhibited an endothermic peak near about at 140.7° C. in differential scanning calorimetry.

Example 2

Receptor Binding at the 5HT$_{1A}$ Receptor
1. Materials and Methods
1.1 Test Compound
  7-{4-[4-(2,3-Dichlorophenyl)-1-piperazinyl]-butoxy-3,4-dihydrocarbostyril (aripiprazole) was used as test compound.

1.2 Reference Compounds

Serotonin (5-HT) and WAY-100635 (N-[2-[4-(2-methoxyphenyl)-1-piperazinyl]ethyl]-N-(2-pyridyl)-cyclohexanecarboxamide, a 5-HT$_{1A}$ receptor antagonist, manufactured by RBI (Natick, Mass.) were used as reference compounds.

1.3 Vehicle

Dimethyl sulfoxide (DMSO) manufactured by Sigma Chemical Co. (St. Louis, Mo.) was used as vehicle.

1.4 Preparation of Test and Reference Compounds

Test compound was dissolved in 100% dimethyl sulfoxide (DMSO) to yield 100 µM stock solutions (final concentration of DMSO in all tubes containing test compound was 1%, v/v). All other reference compounds were prepared by the same method using double-distilled water rather than DMSO.

1.5 Experimental Procedure for the [$^{35}$S]GTPγS Binding Assay

Test and reference compounds were studied in triplicate at 10 different concentrations (0.01, 0.1, 1, 5, 10, 50, 100, 1000, 10000 and 50000 nM) for their effects upon basal [$^{35}$S]GTPγS binding to h5-HT$_{1A}$ CHO cell membranes. Reactions were performed in 5 ml glass test tubes containing 8 µl of test/reference drug mixed with 792 µl of buffer (25 mM Tris HCl, 50 mM NaCl, 5 mM MgCl$_2$, 0.1 mM EGTA, pH=7.4) containing GDP (1 µM), [$^{35}$S]GTPS (0.1 nM) and h5-HT$_{1A}$ CHO cell membranes (10 µg protein/reaction; NEN Life Science Products, Boston, Mass.; catalog #CRM035, lot #501-60024, GenBank # X13556). Reactions proceeded for 60 min at room temperature and were terminated by rapid filtration through Whatman GF/B filter paper, using a Brandel harvester and 4×3 ml ice-cold buffer washes. S radioactivity bound to the filter paper was measured using liquid scintillation counting (1272 Clinigamma, LKB/Wallach).

1.6 Experimental Procedure to Determine the Binding Affinity of the Test compound Aripiprazole at the h5-HT$_{1A}$ Receptor Test compound was studied in triplicate at 10 different concentrations (0.01, 0.1, 1, 10, 50,100, 500, 1000, 5000 and 10000 nM) to determine its displacement of [$^3$H]8-OH-DPAT (1 nM; NEN Life Sciences; catalog #NET 929, lot #3406035, Specific Activity=124.9 Ci/mmol) binding to h5-HT$_{1A}$ receptors in CHO cell membranes (15-20 µg protein; NEN Life Science Products, catalog #CRM035, lot #501-60024). Membranes (396 µl) were incubated in 5 ml glass tubes containing [$^3$H]8-OH-DPAT (396 µl), test compound or vehicle (8 µl) and buffer A (50 mM Tris.HCl, 10 mM MgSO$_4$, 0.5 mM EDTA, 0.1% (w/v) ascorbic acid, pH=7.4). All assays proceeded for 60 min at room temperature and were terminated by rapid filtration through Whatman GF/B filter paper (pre-soaked in buffer B; 50 mM Tris.HCl, pH=7.4), using a Brandel harvester and 4×1 ml ice-cold washes with buffer B. Non-specific binding was determined in the presence of 10 µM (+)8-OH-DPAT.

1.7 Parameters Determined

Serotonin (5-HT) is a full 5-HT$_{1A}$ receptor agonist which stimulates increases in basal [$^{35}$S]GTPγS binding to h5-HT$_{1A}$ receptors in recombinant CHO cell membranes. The test compound was studied at 10 concentrations to determine effects upon basal [$^{35}$S]GTPγS binding relative to that produced by 10 µM 5-HT. The relative potency (EC$_{50}$, 95% confidence interval) and intrinsic agonist activity (% of E$_{max}$ for 10 µM 5-HT) was calculated for each compound by computerized non-linear regression analysis of complete concentration-effect data. The binding affinity of test compound at the h5-HT$_{1A}$ receptor was determined by its ability to prevent [$^3$H]8-OH-DPAT binding to CHO cell membranes that express this receptor. Non-linear regression analysis of the competition binding data was used to calculate an inhibition constant (IC$_{50}$, 95% confidence interval), which is the concentration of test compound that occupies half of the h5-HT$_{1A}$ sites specifically bound by [$^3$H]8-OH-DPAT. The affinity of h5-HT$_{1A}$ receptors for test compound (Ki, 95% confidence interval) was calculated by the equation, Ki=(IC$_{50}$)/(1+([[$^3$H] 8-OH-DPAT]/Kd), where the Kd for [$^3$H]8-OH-DPAT at h5-HT$_{1A}$=0.69 nM (NEN Life Sciences). All estimates of drug binding affinity, potency and intrinsic efficacy at the h5-HT$_{1A}$ receptor were calculated using GraphPad Prism version 3.00 for Windows (GraphPad Software, San Diego, Calif.).

2. Results

The test compound and 5-HT produced concentration-dependent increases above basal [$^{35}$S]GTPγS binding. 1% DMSO tested alone had no effect upon basal or drug-induced [$^{35}$S]GTPγS binding.

The test compound (EC$_{50}$=2.12 nM), 5-HT (EC$_{50}$=3.67 nM), potently stimulated basal [$^{35}$S]GTPγS binding. Potency and intrinsic agonist efficacy estimates were derived by non-linear regression analysis with correlation coefficients (r$^2$)>0.98 in each case (Table 1). The test compound exerted partial agonist efficacies in the 65-70% range. WAY-100635 produced no significant change (unpaired Student's t-test) in basal [$^{35}$S]GTPγS 5 binding at all concentrations tested (Table 1). WAY-100635 did, however, completely inhibit the effects of 5-HT and test compound upon [$^{35}$S]GTPγS binding to h5-HT$_{1A}$ receptors in CHO cell membranes (Table 2). Tables 1 and 2 are shown below.

The test compound demonstrated high affinity binding to h5-HT$_{1A}$ receptors in CHO cell membranes (IC$_{50}$4.03 nM, 95% confidence interval=2.67 to 6.08 nM; Ki=1.65 nM, 95% confidence interval=1.09 to 2.48.

TABLE 1

Potency (EC$_{50}$) and Intrinsic Agonist Efficacy (E$_{max}$) of Test compound and Reference Drugs in a h5-HT$_{1A}$[$^{35}$S]GTPγS CHO-cell Membrane Binding Assay.

| Drug | EC$_{50}$, nM (95% Confidence Interval) | E$_{max}$ (% ± SEM) | Goodness of Fit (r$^2$) |
|---|---|---|---|
| Test Compound | 2.12 (0.87 to 5.16) | 68.13 ± 3.16 | 0.986 |
| 5-HT | 3.67 (1.56 to 8.63) | 98.35 ± 4.47 | 0.986 |
| WAY-100635 | — | — | — |

TABLE 2

Inhibitory Potency (IC$_{50}$) of WAY-100635 versus 1 µM Concentration of 5-HT and Test compound in a h5-HT$_{1A}$[$^{35}$S]GTPγS CHO-cell Membrane Binding Assay.

| Drug Combination | WAY-100635 Inhibition Potency, IC$_{50}$, nM (95% Confidence Interval) | Goodness of Fit (r$^2$) |
|---|---|---|
| 5-HT + WAY-100635 | 217.1 (127.4 to 369.7) | 0.988 |
| Test Compound + WAY-100635 | 392.2 (224.1 to 686.2) | 0.989 |

Example 3

Formulation Examples

Several non-limiting formulation examples of aripiprazole or dehydroaripiprazole with mood stabilizers are presented below.

Formulation Sample Example 1

| | |
|---|---|
| Anhydrous Aripiprazole Crystals B | 5 mg |
| Lithium | 600 mg |
| Starch | 131 mg |
| Magnesium stearate | 4 mg |
| Lactose | 60 mg |
| Total | 800 mg |

According to a preparation method which is well-known to a person having an ordinary skill in the art, the tablet containing the above mentioned formulation is prepared.

Formulation Sample Example 2

| | |
|---|---|
| Anhydrous Aripiprazole Crystals B | 5 mg |
| Valproic Acid | 1000 mg |
| Starch | 131 mg |
| Magnesium stearate | 4 mg |
| Lactose | 60 mg |
| Total | 1200 mg |

According to a common method, the tablet containing the above mentioned formulation is prepared.

Formulation Sample Example 3

| | |
|---|---|
| Anhydrous Aripiprazole Crystals B | 5 mg |
| Divalproex sodium | 750 mg |
| Starch | 131 mg |
| Magnesium stearate | 4 mg |
| Lactose | 60 mg |
| Total | 950 mg |

According to a common method, the tablet containing the above mentioned formulation is prepared.

Formulation Sample Example 4

| | |
|---|---|
| Anhydrous Aripiprazole Crystals B | 5 mg |
| Carbamazepine | 500 mg |
| Starch | 131 mg |
| Magnesium stearate | 4 mg |
| Lactose | 60 mg |
| Total | 700 mg |

According to a common method, the tablet containing the above mentioned formulation is prepared.

Formulation Sample Example 5

| | |
|---|---|
| Anhydrous Aripiprazole Crystals B | 5 mg |
| Oxcarbamazepine | 800 mg |
| Starch | 131 mg |
| Magnesium stearate | 4 mg |
| Lactose | 60 mg |
| Total | 1000 mg |

According to a common method, the tablet containing the above mentioned formulation is prepared.

Formulation Sample Example 6

| | |
|---|---|
| Anhydrous Aripiprazole Crystals B | 5 mg |
| Zonisamide | 300 mg |
| Starch | 131 mg |
| Magnesium stearate | 4 mg |
| Lactose | 60 mg |
| Total | 500 mg |

According to a common method, the tablet containing the above mentioned formulation is prepared.

Formulation Sample Example 7

| | |
|---|---|
| Anhydrous Aripiprazole Crystals B | 5 mg |
| Lamotragine | 250 mg |
| Starch | 131 mg |
| Magnesium stearate | 4 mg |
| Lactose | 60 mg |
| Total | 450 mg |

According to a common method, the tablet containing the above mentioned formulation is prepared.

Formulation Sample Example 8

| | |
|---|---|
| Anhydrous Aripiprazole Crystals B | 5 mg |
| Topiramate | 250 mg |
| Starch | 131 mg |
| Magnesium stearate | 4 mg |
| Lactose | 60 mg |
| Total | 450 mg |

According to a common method, the tablet containing the above mentioned formulation is prepared.

Formulation Sample Example 9

| | |
|---|---|
| Anhydrous Aripiprazole Crystals B | 5 mg |
| Gabapentin | 800 mg |
| Starch | 131 mg |
| Magnesium stearate | 4 mg |
| Lactose | 60 mg |
| Total | 1000 mg |

According to a common method, the tablet containing the above mentioned formulation is prepared.

Formulation Sample Example 10

| | |
|---|---|
| Anhydrous Aripiprazole Crystals B | 5 mg |
| Levetiracetam | 600 mg |
| Starch | 131 mg |
| Magnesium stearate | 4 mg |
| Lactose | 60 mg |
| Total | 800 mg |

According to a common method, the tablet containing the above mentioned formulation is prepared.

Several non-limiting formulation examples of dehydroaripiprazole and mood stabilizers are presented below. It is to be understood that any one of DM-1458, DM-1451, DM-1452, DM-1454 or DCPP, as shown in FIG. 8, could be substituted for dehydroaripiprazole in these disclosed formulations.

Formulation Sample Example 11

| | |
|---|---|
| Dehydroaripiprazole | 5 mg |
| Lithium | 600 mg |
| Starch | 131 mg |
| Magnesium stearate | 4 mg |
| Lactose | 60 mg |
| Total | 800 mg |

According to a preparation method which is well-known to a person having an ordinary skill in the art, the tablet containing the above mentioned formulation is prepared.

Formulation Sample Example 12

| | |
|---|---|
| Dehydroaripiprazole | 5 mg |
| Valproic Acid | 1000 mg |
| Starch | 131 mg |
| Magnesium stearate | 4 mg |
| Lactose | 60 mg |
| Total | 1200 mg |

According to a common method, the tablet containing the above mentioned formulation is prepared.

Formulation Sample Example 13

| | |
|---|---|
| Dehydroaripiprazole | 5 mg |
| Divalproex sodium | 750 mg |
| Starch | 131 mg |
| Magnesium stearate | 4 mg |
| Lactose | 60 mg |
| Total | 950 mg |

According to a common method, the tablet containing the above mentioned formulation is prepared.

Formulation Sample Example 14

| | |
|---|---|
| Dehydroaripiprazole | 5 mg |
| Carbamazepine | 500 mg |
| Starch | 131 mg |
| Magnesium stearate | 4 mg |
| Lactose | 60 mg |
| Total | 700 mg |

According to a common method, the tablet containing the above mentioned formulation is prepared.

Formulation Sample Example 15

| | |
|---|---|
| Dehydroaripiprazole | 5 mg |
| Oxcarbamazepine | 800 mg |
| Starch | 131 mg |
| Magnesium stearate | 4 mg |
| Lactose | 60 mg |
| Total | 1000 mg |

According to a common method, the tablet containing the above mentioned formulation is prepared.

Formulation Sample Example 16

| | |
|---|---|
| Dehydroaripiprazole | 5 mg |
| Zonisamide | 300 mg |
| Starch | 131 mg |
| Magnesium stearate | 4 mg |
| Lactose | 60 mg |
| Total | 500 mg |

According to a common method, the tablet containing the above mentioned formulation is prepared.

Formulation Sample Example 17

| | |
|---|---|
| Dehydroaripiprazole | 5 mg |
| Lamotragine | 250 mg |
| Starch | 131 mg |
| Magnesium stearate | 4 mg |
| Lactose | 60 mg |
| Total | 450 mg |

According to a common method, the tablet containing the above mentioned formulation is prepared.

Formulation Sample Example 18

| | |
|---|---|
| Dehydroaripiprazole | 5 mg |
| Topiramate | 250 mg |
| Starch | 131 mg |
| Magnesium stearate | 4 mg |
| Lactose | 60 mg |
| Total | 450 mg |

According to a common method, the tablet containing the above mentioned formulation is prepared.

Formulation Sample Example 19

| Dehydroaripiprazole | 5 mg |
|---|---|
| Gabapentin | 800 mg |
| Starch | 131 mg |
| Magnesium stearate | 4 mg |
| Lactose | 60 mg |
| Total | 1000 mg |

According to a common method, the tablet containing the above mentioned formulation is prepared.

Formulation Sample Example 20

| Dehydroaripiprazole | 5 mg |
|---|---|
| Levetiracetam | 600 mg |
| Starch | 131 mg |
| Magnesium stearate | 4 mg |
| Lactose | 60 mg |
| Total | 800 mg |

According to a common method, the tablet containing the above mentioned formulation is prepared.

Formulation Sample Example 21

| Anhydrous Aripiprazole Crystals B | 5 mg |
|---|---|
| clonazepam | 600 mg |
| Starch | 131 mg |
| Magnesium stearate | 4 mg |
| Lactose | 60 mg |
| Total | 800 mg |

According to a common method, the tablet containing the above mentioned formulation is prepared.

Formulation Sample Example 22

| Dehydroaripiprazole | 5 mg |
|---|---|
| clonazepam | 600 mg |
| Starch | 131 mg |
| Magnesium stearate | 4 mg |
| Lactose | 60 mg |
| Total | 800 mg |

According to a common method, the tablet containing the above mentioned formulation is prepared.

Example 4

Method of Treatment of Patients with a New Diagnosis, Recurrent or Refractory Episode of Bipolar Disorder (I or II) with or without psychotic features, manic or mixed episode as defined by DSM -IV-R criteria.

A combination of aripiprazole, or an aripiprazole metabolite, and at least one mood stabilizer is evaluated as a therapy for patients with a new diagnosis, recurrent or refractory episode of bipolar disorder (I or II), acute mania, or bipolar depression. Patients ranging in age from 18 to 65 years who are diagnosed with bipolar disorder (I or II), acute mania, or bipolar depression are evaluated to ensure that they have a baseline Young Mania Rating Scale (YMRS) score of greater than 24. Only patients with this YMRS score receive treatment. These patients are interviewed to obtain a complete medical and psychiatric history. Aripiprazole, or an aripiprazole metabolite, is first administered at a dose of 10 mg/day and increased to 30 mg/day as needed in the opinion of the monitoring psychiatrist. Aripiprazole, or an aripiprazole metabolite, is administered to these patients at a dose of from 10 mg/day to 30 mg/day for a period of at least four weeks, and up to eight weeks for patients who respond well to this treatment during the first four weeks. The aripiprazole, or the aripiprazole metabolite, is administered together with at least one mood stabilizer, wherein the mood stabilizer is lithium, valproic acid, divalproex sodium, carbamazapine, oxcarbamazapine, zonisamide, lamotragine, topiramate, gabapentin, levetiracetam or clonazepam.

The aripiprazole, or the aripiprazole metabolite, can be administered in one dosage form, for example a tablet, and the mood stabilizer may be administered in a separate dosage form, for example a tablet. The administration may occur at about the same time or at different times during the day. Dosages may be within the ranges provided above for each of aripiprazole, an aripiprazole metabolite and for the mood stabilizer.

Alternatively, a dosage form containing aripiprazole, or an aripiprazole metabolite, in administered in combination with at least one mood stabilizer and a pharmaceutically acceptable carrier. Such combinations include without limitation the following: aripiprazole/lithium, aripiprazole/valproic acid, aripiprazole/divalproex sodium, aripiprazole/carbamazapine, aripiprazole/oxcarbamazapine, aripiprazole/zonisamide, aripiprazole/lamotragine, aripiprazole/topiramate, aripiprazole/gabapentin, aripiprazole/levetiracetam and aripiprazole/clonazepam. An improvement in alleviation of symptoms of bipolar disorder (I or II), acute mania, or bipolar depression is observed in these patients following administration of aripiprazole, or aripiprazole metabolite, and the one or more mood stabilizers, as shown by results of testing performed during and after the duration of administration of aripiprazole, or an aripiprazole metabolite, and the mood stabilizer. The YMRS and other measures such as CGI, AIMS, SAS, Simpson & Angus and Barnes, commonly known to one of ordinary skill in the art, are administered to these patients. Results demonstrate a normalization of mood.

Example 5

Efficacy of Aripiprazole in combination with valproate or lithium in the treatment of mania in patients partially nonresponsive to valproate or lithium monotherapy.

A 6-week double-blind, randomized, placebo-controlled trial is conducted to determine the efficacy of combined therapy with aripiprazole and either valproate or lithium compared with valproate or lithium alone in treating acute manic or mixed bipolar episodes. The methods used are generally as described in Tohen et al., (Arch. Gen. Psychiatry, 2002 January; 59(1):62-9). The objective is to evaluate the efficacy of aripiprazole (1-30 mg/day) vs placebo when added to ongoing mood-stabilizer therapy as measured by reductions in Young Mania Rating Scale (YMRS) scores. Patients with bipolar disorder, manic or mixed episode, who are inadequately responsive to more than 2 weeks of lithium (600 mg/day) or valproate (500 mg/day) therapy, are randomized to receive cotherapy (aripiprazole+mood-stabilizer) or monotherapy (placebo+mood-stabilizer). The results indicate that aripiprazole cotherapy improves patients' YMRS total scores more than monotherapy. Clinical response rates (> or =50% improvement on YMRS) are higher with cotherapy. Aripiprazole cotherapy improves 21-item Hamilton Depression Rating Scale (HAMD-21) total scores more than monotherapy. In patients with mixed-episodes with moderate to severe depressive symptoms (DSM-IV mixed episode; HAMD-21 score of > or =20 at baseline), aripiprazole cotherapy improves HAMD-21 scores compared to monotherapy. Extrapyramidal symptoms (Simpson-Angus Scale, Barnes Akathisia Scale, Abnormal Involuntary Movement Scale) are not significantly changed from baseline to end point in either treatment group. Compared with the use of valproate or lithium alone, the addition of aripiprazole provided superior efficacy in the treatment of manic and mixed bipolar episodes.

Example 6

Efficacy of Dehydroaripiprazole in combination with valproate or lithium in the treatment of mania in patients partially nonresponsive to valproate or lithium monotherapy.

A 6-week double-blind, randomized, placebo-controlled trial is conducted to determine the efficacy of combined therapy with dehydroaripiprazole and either valproate or lithium, compared with valproate or lithium alone, in treating acute manic or mixed bipolar episodes. The methods used are generally as described in Tohen et al., (Arch. Gen. Psychiatry, 2002 January; 59(1):62-9). The objective is to evaluate the efficacy of dehydroaripiprazole (1-30 mg/day) vs placebo when added to ongoing mood-stabilizer therapy as measured by reductions in Young Mania Rating Scale (YMRS) scores. Patients with bipolar disorder, manic or mixed episode, who are inadequately responsive to more than 2 weeks of lithium (600 mg/day) or valproate (500 mg/day) therapy, are randomized to receive cotherapy (dehydroaripiprazole+mood-stabilizer) or monotherapy (placebo+mood-stabilizer). The results indicate that dehydroaripiprazole cotherapy improves patients' YMRS total scores more than monotherapy. Clinical response rates (> or =50% improvement on YMRS) are higher with cotherapy. Dehydroaripiprazole cotherapy improves 21-item Hamilton Depression Rating Scale (HAMD-21) total scores more than monotherapy. In patients with mixed-episodes with moderate to severe depressive symptoms (DSM-IV mixed episode; HAMD-21 score of > or =20 at baseline), dehydroaripiprazole cotherapy improves HAMD-21 scores compared to monotherapy. Extrapyramidal symptoms (Simpson-Angus Scale, Barnes Akathisia Scale, Abnormal Involuntary Movement Scale) are not significantly changed from baseline to end point in either treatment group. Compared with the use of valproate or lithium alone, the addition of dehydroaripiprazole provided superior efficacy in the treatment of manic and mixed bipolar episodes.

Example 7

A double-blind, randomized, placebo-controlled study of Aripiprazole as adjunctive treatment for adolescent mania.

This randomized, double-blind, placebo-controlled study examines the efficacy and tolerability of aripiprazole in combination with divalproex (DVP) for acute mania in adolescents with bipolar disorder. The methods employed are essentially as described by Delbello et al., (J. Am. Acad. Child Adolesc. Psychiatry, 2002 October; 41(10):1216-23). It is hypothesized that DVP in combination with aripiprazole is more effective than DVP alone for treating mania associated with adolescent bipolar disorder. Thirty manic or mixed bipolar I adolescents (12-18 years) receive an initial DVP dose of 20 mg/kg and are randomly assigned to 6 weeks of combination therapy with aripiprazole, about 10 mg/day or placebo. Primary efficacy measures are change from baseline to endpoint in Young Mania Rating Scale (YMRS) score and YMRS response rate. Safety and tolerability are assessed weekly. The DVP+aripiprazole group demonstrates a greater reduction in YMRS scores from baseline to endpoint than the DVP+placebo group. Moreover, YMRS response rate is significantly greater in the DVP+aripiprazole group than in the DVP+placebo group. No significant group differences from baseline to endpoint in safety measures are noted. Sedation, rated as mild or moderate, is more common in the DVP+aripiprazole group than in the DVP+placebo group. The results indicate that aripiprazole in combination with DVP is more effective for the treatment of adolescent bipolar mania than DVP alone. In addition, the results suggest that aripiprazole is well tolerated when used in combination with DVP for the treatment of mania.

Example 8

A double-blind, randomized, placebo-controlled study of Dehydroaripiprazole as adjunctive treatment for adolescent mania.

This randomized, double-blind, placebo-controlled study examines the efficacy and tolerability of dehydroaripiprazole in combination with divalproex (DVP) for acute mania in adolescents with bipolar disorder. The methods employed are essentially as described by Delbello et al., (J. Am. Acad. Child Adolesc. Psychiatry, 2002 October; 41(10):1216-23). It is hypothesized that DVP in combination with dehydroaripiprazole is more effective than DVP alone for treating mania associated with adolescent bipolar disorder. Thirty manic or mixed bipolar I adolescents (12-18 years) receive an initial DVP dose of 20 mg/kg and are randomly assigned to 6 weeks of combination therapy with dehydroaripiprazole, about 10 mg/day or placebo. Primary efficacy measures are change from baseline to endpoint in Young Mania Rating Scale (YMRS) score and YMRS response rate. Safety and tolerability are assessed weekly. The DVP+dehydroaripiprazole group demonstrates a greater reduction in YMRS scores from baseline to endpoint than the DVP+placebo group. Moreover, YMRS response rate is significantly greater in the DVP+dehydroaripiprazole group than in the DVP +placebo group. No significant group differences from baseline to endpoint in safety measures are noted. Sedation, rated as mild or moderate, is more common in the DVP+dehydroaripiprazole group than in the DVP+placebo group. The results indicate that dehydroaripiprazole in combination with DVP is more effective for the treatment of adolescent bipolar mania than DVP alone. In addition, the results suggest that aripiprazole is well tolerated when used in combination with DVP for the treatment of mania.

All patents, patent applications, scientific and medical publications mentioned herein are hereby incorporated in their entirety. It should be understood, of course, that the foregoing relates only to preferred embodiments of the present invention and that numerous modifications or alterations may be made therein without departing from the spirit and the scope of the invention as set forth in the appended claims.

The invention claimed is:

1. A method of treating bipolar disorder in a patient partially nonresponsive to lithium or valproic acid, divalproex sodium or a salt thereof monotherapy comprising:
    administering an amount of a composition comprising aripiprazole, and lithium or a salt thereof in a pharmaceutically acceptable carrier, wherein the amount of lithium is about 0.01 to 500 parts by weight and the amount of aripiprazole is about 1 part by weight,
    wherein the bipolar disorder is chosen from bipolar disorder I, bipolar disorder II, bipolar disorder with or without psychotic features, mania, acute mania, bipolar depression, and mixed episodes.

2. A method of treating bipolar disorder in a patient partially nonresponsive to lithium or valproic acid, divalproex sodium or a salt thereof monotherapy comprising:
    administering separately a first amount of aripiprazole, and a second amount of lithium, wherein the amount of lithium is about 0.01 to 500 parts by weight and the amount of aripiprazole is about 1 part by weight,
    wherein the bipolar disorder is chosen from bipolar disorder I, polar disorder II, bipolar disorder with or without psychotic features, mania, acute mania, bipolar depression, and mixed episodes.

3. The method of claim 1, wherein aripiprazole is anhydrous aripiprazole crystals B.

4. The method of claim 1, wherein the bipolar disorder is bipolar disorder I.

5. The method of claim 1, wherein the bipolar disorder is mania with bipolar disorder I.

6. The method of claim 2, wherein the bipolar disorder is bipolar disorder II.

7. The method of claim 2, wherein the bipolar disorder is mania with bipolar disorder I.

8. The method of claim 1, wherein the bipolar disorder is mixed episode associated with bipolar disorder I.

9. The method of claim 2, wherein the bipolar disorder is mixed episode associated with bipolar disorder I.

10. The method of claim 2, wherein aripiprazole is anhydrous aripiprazole crystals B.

* * * * *